United States Patent [19]

Kampe et al.

[11] Patent Number: 4,824,846

[45] Date of Patent: Apr. 25, 1989

[54] 2-AZOLYLMETHYL-2-ARYL-1,3-DIOXO-LANES AND THE SALTS THEREOF, AGENTS CONTAINING SAME, AND THE USE THEREOF

[75] Inventors: Klaus D. Kampe, Bad Soden am Taunus; Wolfgang Raether, Dreieich; Walter Dittmar, Hofheim am Taunus; Heinz Hänel, Bad Homburg, all of Fed. Rep. of Germany

[73] Assignee: Hoechst Aktiengesellschaft, Frankfurt am Main, Fed. Rep. of Germany

[21] Appl. No.: 28,087

[22] Filed: Mar. 19, 1987

[30] Foreign Application Priority Data

Mar. 21, 1986 [DE] Fed. Rep. of Germany ........ 3609596

[51] Int. Cl.$^4$ .................. A61K 31/505; C07D 405/14
[52] U.S. Cl. .................... 514/252; 514/254; 544/237; 544/252; 544/253; 544/283; 544/295; 544/363; 544/364
[58] Field of Search ...................... 544/295, 283, 252; 514/254, 252

[56] References Cited

U.S. PATENT DOCUMENTS 4,287,195 9/1981 Heeres et al. ...................... 514/252

*Primary Examiner*—Richard L. Raymond
*Assistant Examiner*—James H. Turnipseed
*Attorney, Agent, or Firm*—Finnegan, Henderson, Farabow, Garrett, & Dunner

[57] ABSTRACT

Compounds I

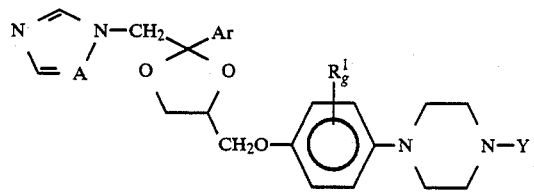

where A equals CH or N; Ar equals naphthyl, thienyl or phenyl; $R^1$ equals alkyl, F or Cl; g equals zero, 1 or 2; and Y equals various heterocyclic bases, and the acid-addition salts thereof, are described.

Several preparation processes are described.

The compounds IIIa

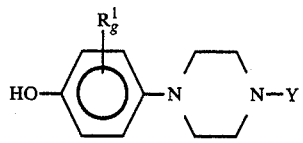

where $R^1$, g and Y are as specified in the case of the formula I, serve as intermediates for the preparation of these compounds. Processes are also specified for the preparation of IIIa.

I represent valuable antimycotics.

6 Claims, No Drawings

2-AZOLYLMETHYL-2-ARYL-1,3-DIOXOLANES AND THE SALTS THEREOF, AGENTS CONTAINING SAME, AND THE USE THEREOF

The invention relates to 2-azolylmethyl-2-aryl-4-[(4-piperazinophenoxy)methyl]-1,3-dioxolanes, including the salts thereof, which are substituted by heterocyclic rings, processes for the preparation thereof, medicaments containing these compounds, and the use thereof, particularly as antimycotics.

2-Azolymethyl-2-aryl-4-[(4-piperazinophenoxy)methyl]-1,3-dioxolanes which have an antimycotic or fungicidal action are already known and are described, inter alia, in German Offenlegungsschrift No. 2,804,096 and European Published Application No. 7,696. The best known representatives from the large number of compounds described are 2-S,(R)-(2,4-dichlorophenyl)-2-(imidazol-1-ylmethyl)-4-R,)S)-[4-(4-acetylpiperazin-1-yl)phenoxymethyl]-1,3-dioxolane (ketoconazole) and 2-S,(R)-(2,4-dichlorophenyl)-2-(1,2,4-triazol-1-ylmethyl)-4-R,(S)-[4-isopropylpiperazin-1-yl)phenoxymethyl]-1,3-dioxolane (terconazole), which are commercially available as antimycotics (cf. German Offenlegungsschrift No. 2,804,096, Example 20 and Example 53), ketoconazole being used mainly as a systemically active antimycotic and terconazole as a topically active antimycotic. However, the antimycotic action and, in particular, the toleration of the known compounds are not always completely satisfactory.

It has now been found that 2-azolylmethyl-2-aryl-4-[(4-piperazinophenoxy)methyl]-1,3-dioxolanes of the formula

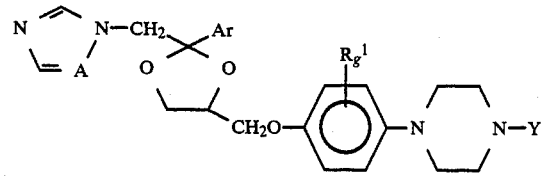

I in which
A denotes CH or N,
Ar denotes naphthyl, thienyl, halothienyl or a phenyl group which is unsubstituted or carries one to 3 substituents, where the substituents may be identical or different and denote halogen, trifluoromethyl, $C_1$-$C_2$-alkyl, $C_1$-$C_2$-alkoxy or phenoxy,
$R^1$ denotes $C_1$-$C_3$-alkyl, F or Cl,
g denotes 0, 1 or 2 and
y denotes the following heterocyclic radicals

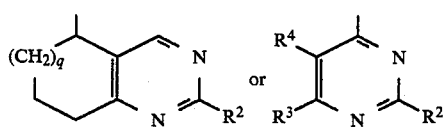

(a)

in which $R^2$ denotes $C_1$-$C_4$-alkyl, a phenyl group which is unsubstituted or carries 1 or 2 substituents, where the substituents may be identical or different and denote halogen, trifluoromethyl, methoxy, ethoxy, nitro or $C_1$-$C_4$-alkyl, or a phenyl-$C_1$-$C_2$-alkyl group which is unsubstituted or carries 1 ot 2 substituents in the phenyl radical, where the substituents may be identical or different and denote F, Cl, methoxy, ethoxy of $C_1$-$C_3$-alkyl,
$R^3$ denotes H, $C_1$-$C_8$-alkyl, $C_3$-$C_6$-cycloalkyl-$C_1$-$C_3$-alkyl, a phenyl group which is unsubstituted or carries 1 or 2 substituents, where the substituents may be identical or different and denote halogen, methoxy, ethoxy or $C_1$-$C_3$-alkyl, a phenyl-$C_1$-$C_2$-alkyl group which is unsubstituted or substituted in the phenyl radical by methoxy, 1,2-methylenedioxy, F, Cl or $C_1$-$C_3$-alkyl, or trifluoromethyl,
$R^4$ denotes H, $C_1$-$C_4$-alkyl or benzyl, or $R^3$ and $R^4$ together denote —$(CH_2)_r$—, where r is 3 or 4, or —CH=CH—CH=CH—, and
q denotes 0 or 1, or

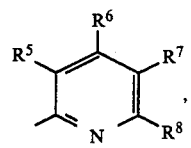

(b)

in which
$R^5$ denotes H or CN,
$R^6$ denotes H, $C_1$-$C_4$-alkyl, or a phenyl group which is unsubstituted or substituted by $OCH_3$, F, Cl, $CH_3$ or $C_2H_5$,
$R^7$ denotes H, benzyl, $CF_3$ or $CH_3$,
$R^8$ denotes $C_5$-$C_6$-cycloalkyl, or a phenyl group which is unsubstituted or substituted by $OCH_3$, F, Cl, $CH_3$ or $C_2H_5$, and, if $R^5$ denotes CN and/or $R^7$ denotes $CF_3$, $R^8$ may alternatively denote H, or
$R^7$ and $R^8$ together denote —$(CH_2)_4$—, or

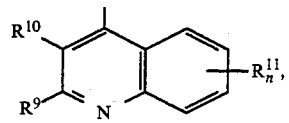

(c)

in which
$R^9$ denotes H, methyl or ethyl,
$R^{10}$ denotes H, CN or $COOR^{12}$, where $R^{12}$ denotes methyl or ethyl,
$R^{11}$ denotes $C_1$-$C_4$-alkyl, $C_1$-$C_4$-alkoxy, halogen or trifluoromethyl, and
n denotes 0, 1 or 2, where, if $R^{11}$ denotes $CF_3$, n is 1, and, if n ≠0, the $R^{11}$ radicals may be in the 5, 6, 7 or 8 position of the quinoline system, or

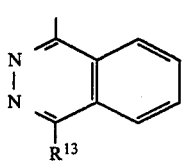

(d)

in which
$R^{13}$ denotes H, $C_1$-$C_4$-alkyl, or a phenyl group which is unsubstituted or carries 1 or 2 substituents, where the substituents may be identical or different and denote halogen, methoxy, ethoxy, methyl or ethyl, and the physiologically acceptable acid-addition salts thereof, have valuable antimycotic or fungicidal properties. They are thus suitable for combating mycosis in humans and animals and for combating fungal infestations in plants and other materials.

In this connection, the term "halothienyl" is taken to mean a thienyl radical which is linked in the 2 or 3 position and which may be substituted in any position by a halogen atom, preferably bromine or chlorine, the terms "$C_1$–$C_3$-, $C_1$–$C_4$- and $C_1$–$C_8$-alkyl" are taken to mean an unbranched or branched hydrocarbon radical having 1–3, 1–4 or 1–8 carbon atoms respectively, the term "$C_3$–$C_6$- or $C_5$–$C_6$-cycloalkyl" is taken to mean a cyclopropyl, cyclobutyl, cyclopentyl or cyclohexyl radical or cyclopentyl or cyclohexyl radical respectively, the term "$C_1$–$C_4$-alkoxy" is taken to mean an alkoxy group the hydrocarbon radical of which has the meaning specified under the term "$C_1$–$C_4$-alkyl", and the term "halogen" is taken to mean an F, Cl, Br or I atom.

Preferred compounds of the formula I are those in which at least one of the substituents or indices has the following meaning:

A denotes CH or N,
Ar denotes a phenyl group which is substituted by 1 or 2 F or Cl atoms,
$R^1$ denotes $CH_3$ or $C_2H_5$,
g denotes 0 or 2, and
where Y denotes the heterocyclic radical a),
$R^2$ denotes $C_1$–$C_4$-alkyl, a phenyl group which is unsubstituted or carries 1 or 2 identical or different substituents, where the substituents denote F, Cl, $OCH_3$, $OC_2H_5$, $CH_3$ or $C_2H_5$, or denotes a benzyl group or a benzyl group which is substituted in the phenyl radical by an F or Cl atom,
$R^3$ denotes $C_1$–$C_8$-alkyl, $C_5$–$C_6$-cycloalkyl-$C_1$–$C_2$-alkyl, or a phenyl group or a phenyl-$C_1$–$C_2$-alkyl group which is in each case unsubstituted or substituted in the phenyl radical by 1 or 2 F, Cl, $OCH_3$ or $CH_3$, or $CF_3$,
$R^4$ denotes $C_1$–$C_4$-alkyl or benzyl, or
$R^3$ and $R^4$ together denote —$(CH_2)_3$—, —$(CH_2)_4$— or —CH=CH—CH=CH—, and
q denotes 0 or 1, or
where
Y denotes the heterocyclic radical (b),
$R^5$ denotes H or CN,
$R^6$ denotes H, $CH_3$ or phenyl,
$R^7$ denotes H or $CF_3$,
$R^8$ denotes phenyl or phenyl which is substituted by F, Cl, $CH_3$ or $OCH_3$, or, if $R^5$ denotes CN and/or $R^7$ denotes $CF_3$, additionally denotes H, and
$R^7$ and $R^8$ together denote —$(CH_2)_4$—, or
where
Y denotes the heterocyclic radical (c),
$R^9$ denotes H,
$R^{10}$ denotes CN, $COOCH_3$ or $COOC_2H_5$,
$R^{11}$ denotes $C_1$–$C_4$-alkyl, $C_2$–$C_4$-alkoxy, F, Cl, Br or $CF_3$, and
n denotes 0, 1 or 2, where, if $R^{11}$ denotes $CF_3$, n=1 and, if n does not equal 0, $R^{11}$ may be in the 5, 6, 7 or 8 position, or
where
Y denotes the heterocyclic radical (d)
$R^{13}$ denotes H, $C_1$–$C_4$-alkyl, or a phenyl group which is unsubstituted or substituted by 1 or 2 F, Cl, $OCH_3$ or $CH_3$.

Particularly preferred compounds of the formula I are those in which at least one of the substituents or indices has the following meaning:

A denotes CH or N,
Ar denotes 2,4-dichlorophenyl,
$R^1$ denotes $CH_3$,
g denotes 0 or 2, and
where Y denotes a heterocyclic radial a),
$R^2$ denotes a phenyl group which is unsubstituted or carries 1 or 2 identical or different substituents, where the substituents denote Cl, $OCH_3$, $OC_2H_5$ or $CH_3$, or denotes a benzyl group or a chlorobenzyl group,
$R^3$ denotes $C_1$–$C_8$-alkyl, $C_5$–$C_6$-cycloalkyl-$C_1$–$C_2$-alkyl, or a phenyl group or phenyl-$C_1$–$C_2$-alkyl group, in each case unsubstituted or substituted in the phenyl radical by 1 ot 2 F, Cl, $OCH_3$ or $CH_3$,
$R^4$ denotes $C_1$–$C_4$-alkyl or benzyl, or
$R^3$ and $R^4$ together denote —$(CH_2)_3$—, —$(CH_2)_4$— or —CH=CH—CH=CH—, and
q denotes 0 or 1, or
where
Y denotes a heterocyclic radical (b),
$R^5$ denotes H or CN,
$R^6$ denotes H or $CH_3$,
$R^7$ denotes H of $CF_3$, and
$R^8$ denotes phenyl, or phenyl which is substituted by Cl or $OCH_3$, or, if $R^5$ denotes CN and/or $R^7$ denotes $CF_3$, additionally denotes H, or
where
Y denotes a heterocyclic radical c),
$R^9$ denotes H,
$R^{10}$ denotes CN, $COOCH_3$ or $COOC_2H_5$,
$R^{11}$ denotes $CH_3$, $C_2H_5$, $OCH_3$, $OC_2H_5$, F, Cl, Br or $CF_3$, and
n denotes 0, 1 or 2, where, if $R^{11}$ denotes $CF_3$, n is 5, 6, 7 or 8 position, or
where
Y denotes a heterocyclic radical d),
$R^{13}$ denotes a phenyl group which is unsubstituted or substituted by 1 or 2 F, Cl, $OCH_3$ or $CH_3$.

The invention furthermore relates to the possible stereoisomers of the formula I, as diastereomer racemates and as pure enantiomers, and the pharmaceutically acceptable salts thereof. In particular, this relates to the stereoisomers which are possible as a result of the 2,4-disubstitution of the 1,3-dioxolane ring; the 2-azolylmethyl group may be located in the cis or trans position to the substituent in the 4 position, the substituted phenoxymethyl group. The cis isomers are included in the preferred compounds according to the invention.

Suitable salts of the compounds of the formula I according to the invention are those with physiologically acceptable inorganic and organic acids, such as, for example, hydrochloric acid, hydrobromic acid, hydroiodic acid, sulfuric acid, phosphoric acid, nitric acid, benzenesulfonic acid, toluenesulfonic acid, sulfamic acid, methylsulfuric acid, acetic acid, propionic acid, oleic acid, palmitic acid, stearic acid, malonic acid, maleic acid, succinic acid, glutaric acid, malic acid, tartaric acid, citric acid, fumaric acid, lactic acid, glycolic acid, pyruvic acid, benzoic acid, toluic acid, glutamic acid, furancarboxylic acid, salicyclic acid, or mandelic acid. Preferred salts are those with physiologically acceptable inorganic acids, strong to medium-strength acidic derivatives of such acids, or with fumaric acid.

The compounds according to the inventin differ from the known, abovementioned azolylmethyl-2-aryl-4-[(4-piperazinophenoxy)methyl]-1,3-dioxolanes which are active against fungi and bacteria essentially through the type of the substituents on the piperazinophenoxymethyl unit in the 4 position of the dioxolane ring and through the additional substitution, optionally present, of the phenyl ring of the phenoxy group in the 4 position. The compounds according to the invention differ from the compounds mentioned in EP-A No. 7,696, to some of which they are similar, either through the type and position of the substituents on the hetercyclic rings or by the different structure of the heterocyclic radicals bonded to the piperazine ring.

Surprisingly, the 2-azolyl-2-aryl-4-[(4-piperazinophenoxy)methyl]-1,3-dioxolanes according to the invention exhibit a broader and better anti-mycotic action than the known 2-azolylmethyl-2-aryl-1,3-dioxolane derivatives and the known 2-S,(R)-(2,4-dichlorophenyl)-2-(imidazol-1-ylmethyl)-4-R,(S)-[4-(4-acetylpiperazin-1-yl)phenoxymethyl]-1,3-dioxolane (ketoconazole).

The invention furthermore relates to a process for the preparation of the compounds of the formula I and the salts thereof, wherein (A) a compound of the formula II

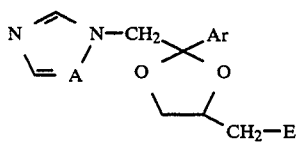

in which
A and Ar have the meanings specified in the case of the formula I and
E denotes halogen, such as F, Cl, Br or I, acyloxy, such as acetoxy, trifluoroacetyloxy, benzoyloxy or nitrobenzoyloxy, alkylsulfonyloxy, such as methanesulfonyloxy, or arylsulfonyloxy, such as benzene-, nitrobenzene-, bromobenzene- or toluenesulfonyloxy,
is reacted with a compound of the formula III

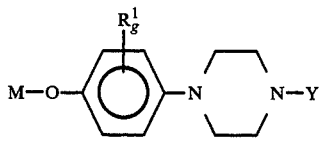

in which
M denotes H, an alkali metal or an alkaline-earth metal, particularly Li, Na or K, or NH$_4$, and
R$^1$, g and Y have the meanings specified in the case of the formula I,
or wherein
(B) a compound of the formula IV,

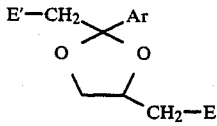

in which
Ar has the meanings specified in the case of the formula I and E and E' have the meanings specified for E in the case of the formula II,
is initially reacted with a compound of the formula III, a compound of the formula V,

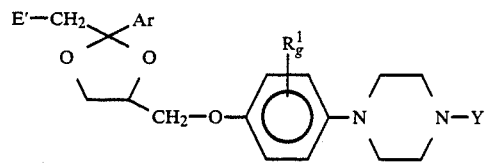

in which
Ar, R$^1$, g and Y have the meanings speified in the case of the formula I, and E' has the meanings specified for E in the case of the formula II,
being prepared here, and a compound of the formula V is subsequently reacted with a compound of the formula VI,

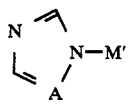

in which A denotes CH or N and
M' denotes H, an alkali metal, an alkaline-earth metal or Si(CH$_3$)$_3$,
or wherein
(C) a compound of the formula VII,

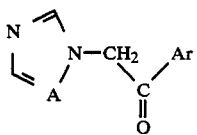

in which A and Ar have the meanings specified in the case of the formula I, is reacted with a 1,2-diol of the formula VIII

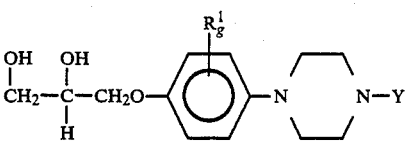

in which R$^1$, g and Y have the meanings specified in the case of the formula I, or wherein
(D) a compound of the formula IX

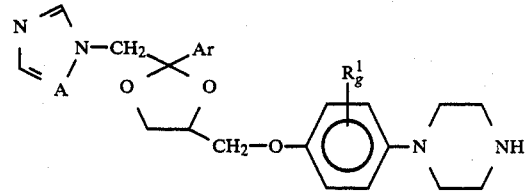

in which A, Ar, R$^1$ and g have the meanings specified in the case of the formula I, is reacted with a compound of the formula X

E''—Y            X in which E'' denotes C$_1$-C$_4$-alkoxy, Cl, Br, I, acyloxy, such as acetyloxy or benzoyloxy, alkylsulfonyloxy, such as methanesulfonyl-oxy, or arylsulfonyloxy, such as benzene-, nitrobenzene- or toluenesulfonyloxy, and Y has the meanings specified undeer a, b, c, and d in the case of formula I, and the compounds of the formula I obtained by routes (A)–(D) are, if appropriate, converted into their physiologically acceptable acid-addition salts using inorganic or organic acids.

In this connection, the term "acyloxy" is taken to mean a straight-chain or branched $C_1$–$C_4$-alkanoyloxy radical, or a benzoyloxy radical which is unsubstituted or substituted in the phenyl nucleus by up to 2 identical or different substituents, where the substituents may denote $CH_3$, $OCH_3$, F, Cl or Br, and the term "arylsulfonyloxy" is taken to mean a phenylsulfonyloxy or naphthysulfonyloxy radical which is unsubstituted or substituted by a Cl, Br, $CH_3$, $C_2H_5$, $OCH_3$, $OC_2H_5$ or $NO_2$.

For the reaction with a compound of the formula IX, any of (a) a compound of the formula $Xa_1$ or of the formula $Xa_2$

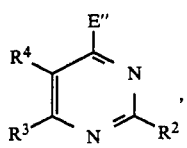

$Xa_1$

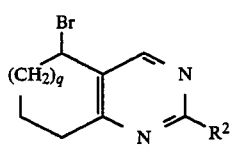

$Xa_2$ in which $R^2$–$R^4$ and q have the meanings specified in the case of formula I, and E" denotes Cl, Br or $OCH_3$, or (b) a compound of the formula Xb,

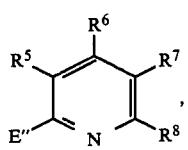

Xb in which $R^5$–$R^8$ have the meanings specified in the case of the formula I, and E" denotes Cl,

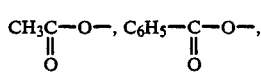

$CH_3SO_2$—O—, 4-$CH_3$—$C_6H_4$—$SO_2$—O— or $C_6H_5$—$SO_2O$—, or (c) a compound of the formula Xc,

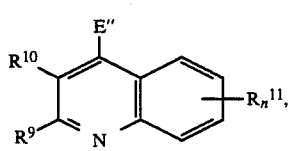

Xc in which $R^9$–$R^{11}$ and n have the meanings specified in the case of the formula I, and E" denotes Cl or Br, or (d) a compound of the formula Xd,

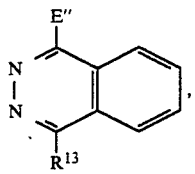

Xd in which $R^{13}$ has the meanings specified in the case of the formula I, and E" denotes cl or $OCH_3$.

Particularly preferred compounds ot the formulae $Xa_1$, Xb, Xc and Xd for the reaction with a compound of the formula IX are those in which E" denotes Cl.

Process version (A), where, in the case of the compounds of the formula II, E preferably denotes Cl, Br, acetoxy, trifluoroacetoxy, methanesulfonyloxy or (substituted) phenylsulfonyloxy, is preferably carried out at a temperature between 20° C. and 180° C., advantageously between 40° C. and 120° C., in the presence of a base and expediently in an inert organic solvent, such as, for example, N,N-dimethylformamide, N,N-dimethylacetamide, dimethyl sulfoxide, N-methyl-2-pyrrolidone, 1,2-dimethoxyethane, dioxane, tetrahydrofuran, 4-methyl-2-pentanone, methanol, ethanol, isopropyl alcohol, propanol, butanol, pentanol, tert.-butyl alcohol, methyl glycol, methylene chloride, acetonitrile or an aromatic hydrocarbon, such as benzene, chlorobenzene, toluene or xylene. Mixtures of the solvents mentioned as examples may also be used.

Suitable bases are, for example, alkali metal or alkaline-earth metal carbonates, hydrogen carbonates, hydroxides, amides, alcoholates or hydrides, such as, for example, sodium carbonate, sodium hydrogen carbonate, potassium carbonate, sodium hydroxide, sodium amide, sodium methylate, potassium t-butylate or sodium hydride, or organic bases, for example teritary amines, such as triethylamine, tributylamine, ethylmorpholine or pyridine, dimethylaminopyridine, quinoline or 1,5-diazabicyclo[5,4,0]undec-5-ene (DBU).

The reaction may likewise be carried out under the conditions of a phase-transfer reaction by allowing the reactants to act on one another in a suitable solvent, such as, for example, ether, dioxane, tetrahydrofuran, methylene chloride, N,N-dimethylformamide, N,N-dimethylacetamide, N-methyl-2-pyrrolidone, butanol, tert.-butanol, an aliphatic, cycloaliphatic or aromatic hydrocarbon, such as hexane, cyclohexane, benzene, toluene or xylene, methyl glycol, anisole or chlorobenzene with vigorous stirring in the presence of a phase-transfer catalyst and either a powdered alkali metal hydroxide, such as, for example, sodium hydroxide or potassium hydroxide, or a concentrated aqueous solution thereof, preferably in a temperature range from 20° C. to 120° C.

Suitable phase-transfer catalysts are, for example, trialkylbenzylammonium or tetraalkylammonium halides, hydroxides or hydrogen sulfates, preferably having 1 to 12 carbon atoms in the alkyl radical, or crown ethers, such as, for example, 12-crown-4, 15-crown-5, 18-crow-6 or dibenzo-18-crown-6.

Preparation of the starting materials:

Some of the starting compounds of the fomula II, in which Ar and A have the meanings specified in the case of the formula I, are known; those which are not known may be prepared analogously to those which are known.

Process version (B), where a compound of the formula IV in which E preferably denotes Br, I, trifluoroacetyloxy, methanesulfonyloxy, benzene-, nitrobenzene-, bromobenzene- or toluenesulfonyloxy, and E″ preferably denotes Cl or Br, is reacted with a compound of the formula III in which M, $R^1$, g and Y have the specified meanings, with formation of a compound of the formula V, is carried out under the same reaction conditions as specified in the case of version A for the preparation of compounds of the formula I.

The preparation of compounds of the formula I by reaction of compounds of the formula V with compounds of the formula VI is expediently carried out in an inert solvent in the presence of a base, in a manner similar to that specified in the case of the first preparation process above, preferably in a temperature range from 100° to 190° C. The reaction is expediently carried out in the presence of an alkali metal iodide, such as, for example, sodium iodide or potassium iodide, if appropriate in an autoclave under pressure.

The reactions described above may expediently be carried out as a one-pot reaction by initially reacting a compound of the formula VI with a compound of the formula III at 40° to 100° C. in the presence of a base in an inert solvent. A compound of the formula VI and, if appropriate, a further mole equivalent of a base and an alkali metal iodide (for example potassium iodide) are subsequently added, without isolation of the compound of the formula V, and the mixture is heated to 100° to 190° C.

Preparation of the starting materials:

Compounds of the formula IV, in which E and E″ have the meanings specified for E in the case of the formula II, are known. They are prepared by converting the hydroxymethyl group in a compound of the formula XI

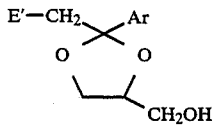

into a reactive ester group in a conventional fashion. Thus, for example, the compounds of the formula IV in which E′ preferably denotes Cl or Br, and E denotes methanesulfonyloxy, are prepared by reacting a compound of the formula XI in which Ar has the meanings specified in the case of the formula I, and E′ denotes Cl or Br, with methanesulfonyl chloride at −10° C. to +50° C., expediently in an inert solvent, in the presence of a base. Compounds of the formula IV in which E, for example, denotes bromine are prepared by reacting compounds of the formula XI (E′=Cl or Br) with brominating agents, such as, for example, $PBr_3$ or $POBr_3$, in an inert solvent at 0° C. to 100° C. These compounds may alternatively be prepared by reacting, by methods which are known for such ketalizations, a compound of the formula XII,

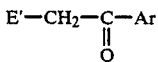

in which E′ denotes Cl or Br, and Ar has the specified meanings, with 1-bromo-2,3-propanediol in an inert solvent in the presence of a strong acid with formation of a 1,3-dioxolane.

The compounds of the formula XI are known.

Process version (C), where a compound of the formula VII is reacted with a compound of the formula VIII with formation of a compound of the formula I, is generally carried out under the same conditions as for the preparation of compounds of the formula IV (version B). The ketalization of ketones of the formula VII using glycerol derivatives of the formula VIII is advantageously carried out in a mixture of solvents comprising an inert solvent which forms an azeotropic mixture with water, such as, for example, benzene, toluene, xylene, chlorobenzene or cyclohexane, and an alcohol, in the presence of a strong acid in a temperature range from 75° to 180° C. At least 2.5 equivalents of a strong acid (relative to the azole compound of the formula VII) and, as alcohols, aliphatic alcohols having a boiling point between 75° and 150° C., and/or monoethers of lower diols, boiling between 100° and 150° C., are advantageously used in this ketalization.

Preparation of the starting materials:

The compounds of the formula VII are known and can be prepared by known methods.

Compounds of the formula VIII, in which $R^1$, g and Y have the meanings specified in the case of the formula I, are prepared by reacting compounds of the formula III with 1-halo-2,3-propanediol in an analogous fashion to that described in Org. Synth. Collect. Vol. I, p. 296.

In process version (D), a compound of the formula IX is reacted with a heterocyclic compound of the formula X, preferably with a heterocyclic compound either of the formula $Xa_1$ or $Xa_2$, or of the formula Xb or Xd, in which E″ in each case has the specified meanings, expediently in an inert organic solvent in a temperature range from 20° to 180° C., preferably from 50° to 120° C. This reaction is advantageously carried out in the presence of a base, which is preferably used in an equimolar amount.

The synthesis of compounds of the formula I from the compounds of the formulae IX and X may alternatively be carried out without adding base. The reactants of the formulae IX and X may be used in different molar ratios, i.e. either the compounds of the formula IX or the compounds of the formula X may be used in excess, but equimolar amounts are advantageously used.

Suitable solvents are, for example, hydrocarbons, ethers in general, such as diethyl ether, 1,2-dimethoxyethane, tetrahydrofuran or dioxane, or acetonitrile, butyronitrile, dimethylformamide, dimethylacetamide, acetone, 4-methyl-2-pentanone, methylene chloride, chloroform, dimethyl sulfoxide, anisole, chlorobenzene or tetrachloroethene, or mixtures of these solvents.

Suitable bases are those described as examples in the case of process version (A).

The reaction may likewise be carried out under the conditions of a phase-transfer reaction, as described in the description of process version (A).

Preparation of the starting materials:

Some of the compounds of the formula IX are known (c.f. German Offenlegungsschrift No. 2,804,096, e.g. Example 21); those which have meanings for Ar which differ from those known and/or in which g denotes 1 or 2 may be prepared analogously to the known compounds (c.f. German Offenlegungsschrift No. 2,804,096).

Some of the compounds of the formula X in which E″ and Y have the specified meanings are known. This applies particularly to compounds of the formula X where E″=Cl.

If the substituents on the heterocyclic compounds Xa₁, Xb, Xc and Xd differ from known compounds and if the substituents are substantially inert, i.e. unreactive, these compounds of the formulae Xa₁Xd, in which the substituents R²–R¹³ and n have the specified meanings, may be prepared analogously to the known compounds of these structures.

The compounds Xa₂ having q=0 or 1 and R² as specified in the case of formula I are prepared from compounds of the formula XI

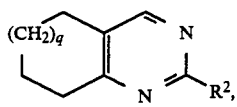   XI in which q and R² have the specified meanings, by bromination using N-bromosuccinimide.

Compounds of the formula Xc in which R¹⁰ denotes COOR¹² and E″, for example, denotes Cl are likewise prepared according to the methods which are conventional for the preparation of compounds of the formula Xc, namely by reaction of compounds of the formula XII,

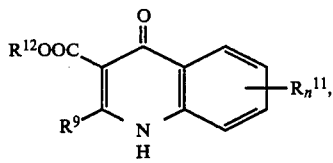   XII in which R⁹, R¹¹, R¹² and n have the specified meanings, with POCl₃ or SOCl₂.

Compounds of the formulae Xa₁ and Xd in which E″ denotes OCH₃ are prepared from appropriate compounds of the formulae Xa₁ and Xd in which E″, for example, denotes Cl by reaction with methanol or with methanol plus up to one equivalent of alkali metal methanolate. Li, Na or K are used as alkali metals.

Depending on the process versions and depending on the temperature range, the reaction times are a few minutes to several hours.

If necessary, the process products can be purified by recrystallization from a suitable solvent or mixture of solvents or by column chromatography on silica gel.

The diastereomeric racemates (cis or trans form) of the compounds of the formula I can be separated in a conventional fashion, for example by selective, fractional crystallization of column chromatography.

Since the stereochemical configuration is already specified in the intermediates of the formula II, the separation into the cis and trans form can be carried out as early as this stage, or even earlier, for example at the stage of the intermediates of the general formula IV, or of the intermediates of the formula IX.

The cis- and trans-diastereomeric racemates can themselves be separated in a conventional fashion into their optical antipodes cis(+), cis(−) or trans(+) and trans(−).

Process versions A, B and D are preferably used for the preparation of compounds of the formula I.

The invention furthermore relates to compounds of the formula IIIa.

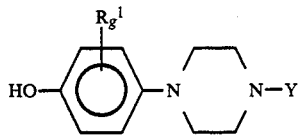   IIIa in which:

$R^1$ denotes $C_1$–$C_3$-alkyl, F or Cl, g denotes 0, 1 or 2, and

Y denotes the following heterocyclic radicals

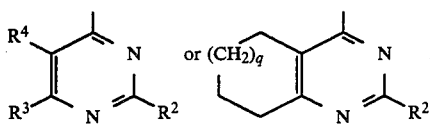   (a)

in which $R^2$ denotes $C_1$–$C_4$-alkyl, a phenyl group which is unsubstituted or carries 1 or 2 substituents, where the substituents may be identical or different and denote halogen, trifluoromethyl, methoxy, ethoxy, nitro or $C_1$–$C_4$-alkyl, or a phenyl-$C_1$–$C_2$-alkyl group which is unsubstituted or carries 1 or 2 substituents in the phenyl radical, where the substituents may be identical or different and denote F, Cl, methoxy, ethoxy or $C_1$–$C_3$-alkyl, $R^3$ denotes H, $C_1$–$C_8$-alkyl, $C_3$–$C_6$-cycloalkyl-$C_1$–$C_3$-alkyl, a phenyl group which is unsubstituted or carries 1 or 2 substituents, where the substituents may be identical or different and denote halogen, methoxy, ethoxy or $C_1$–$C_3$-alkyl, a phenyl-$C_1$–$C_2$-alkyl group which is unsubstituted or substituted in the phenyl radical by methoxy, 1,2-methylenedioxy, F, Cl or $C_1$–$C_3$-alkyl, or denotes trifluoromethyl, $R^4$ denotes H, $C_1$–$C_4$-alkyl or benzyl, or $R^3$ and $R^4$ together debnote —(CH₂)₄—, where r is 3 or 4, or —CH=CH—CH=CH—, and q denotes 0 or 1, or

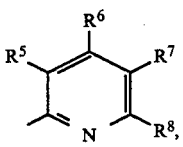

in which $R^5$ denotes H or CN, $R^6$ denotes H, $C_1$–$C_4$-alkyl, or a phenyl group which is unsubstituted or substituted by OCH₃, F, Cl, CH₃ or C₂H₅, $R^7$ denotes H, benzyl or CF₃, $R^8$ denotes $C_5$–$C_6$-cycloalkyl, or a phenyl group which is unsubstituted or substituted by OCH₃, F, Cl, CH₃ or C₂H₅, and, if $R^5$ denotes CN and/or $R^7$ denotes CF₃, $R^8$ may alternatively denote H, or $R^7$ and $R^8$ together denote —(CH₂)₄—, or

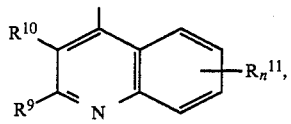

in which
R⁹ denotes H, methyl or ethyl,
R¹⁰ denotes H, CN or COOR¹², where R¹² denotes methyl or ethyl,
R¹¹ denotes $C_1$-$C_4$-alkyl, $C_1$-$C_4$-alkoxy, halogen or trifluoromethyl, and
n denotes 0, 1 or 2, where, if R¹¹ denotes $CF_3$, n is 1, and, if n is not equal to the R¹¹ radicals may be in the 5, 6, 7 or 8 position of the quinoline system, or

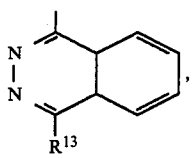

in which
R¹³ denotes H, $C_1$-$C_4$-alkyl, or a phenyl group which is unsubstituted or carries 1 or 2 substituents, where the substituents may be identical or different and denote halogen, methoxy, ethoxy, methyl or ethyl,
and the acid-addition salts thereof.

Preferred compounds of the formula IIIa are those in which at least one of the substituents or indices R¹, g, Y, R²-R¹³, q and n has the following meanings:
R¹ denotes $CH_3$ or $C_2H_5$,
g denotes 0 or 2, and
where Y denotes the heterocyclic radical (a),
R² denotes $C_1$-$C_4$-alkyl, a phenyl group which is unsubstituted or carries 1 or 2 identical or different substituents, where the substituents denote F, Cl, $OCH_3$, $OC_2H_5$, $CH_3$ or $C_2H_5$, or denotes a benzyl group or a benzyl group which is substituted in the phenyl radical by an F or Cl atom,
R³ denotes $C_1$-$C_8$-alkyl, $C_5$-$C_6$-cycloalkyl-$C_1$-$C_2$-alkyl, or a phenyl group or phenyl-$C_1$-$C_2$-alkyl group which is in each case unsubstituted or substituted in the phenyl radical by 1 or 2 F, Cl, $OCH_3$ or $CH_3$, or $CF_3$,
R⁴ denotes $C_1$-$C_4$-alkyl or benzyl, or
R³ and R⁴ together denote —(CH₂)₃—, —(CH₂)₄— or —CH═CH—CH═CH—, and
q denotes 0 or 1, or
where Y denotes the heterocyclic radical (b),
R⁵ denotes H or CN,
R⁶ denotes H, $CH_3$ or phenyl,
R⁷ denotes H, $CH_3$ or $CF_3$,
R⁸ denotes H, $CH_3$, $C_5$-$C_6$-cycloalkyl, phenyl or phenyl which is substituted by F, Cl or $OCH_3$, and/or, if R⁵ denotes CN and/or R⁷ denotes $CF_3$, R⁸ additionally denotes H, or
R⁷ and R⁸ together denote —(CH₂)₄—, or
where Y denotes the heterocyclic radical (c),
R⁹ denotes H,
R¹⁰ denotes CN, $COOCH_3$ or $COOC_2H_5$,
R¹¹ denotes $C_1$-$C_4$-alkyl, $C_1$-$C_4$-alkoxy, F, Cl, Br or $CF_3$, and n denotes 0, 1 or 2, where, if R¹¹ denotes $CF_3$, n=1 and, if n does not equal 0, R¹¹ may be in the 5, 6, 7 or 8 position, or
where Y denotes the heterocyclic radical (d)
R¹³ denotes H, $C_1$-$C_4$-alkyl, or a phenyl group which is unsubstituted or substituted by 1 or 2 F, Cl, $OCH_3$ or $CH_3$.

Particularly preferred compounds of the formula IIIa are those in which at least one of the substituents or indices has the following meaning:
R¹ denotes $CH_3$,
g denotes 0 or 2, and
where Y denotes a heterocyclic radical (a),
R² denotes a phenyl group which is unsubstituted or carries 1 or 2 identical or different substituents, where the substituents denote Cl, $OCH_3$, $OC_2H_5$ or $CH_3$, or denotes benzyl group or a chlorobenzyl group,
R³ denotes $C_1$-$C_8$-alkyl, $C_5$-$C_6$-cycloalkyl-$C_1$-$C_2$-alkyl, or a phenyl group or phenyl-$C_1$-$C_2$-alkyl group, in each case unsubstituted or substituted in the phenyl radical by 1 or 2 F, Cl, $OCH_3$ or $CH_3$,
R⁴ denotes $C_1$-$C_4$-alkyl or benzyl, or
R³ and R⁴ together denote —(CH₂)₃—, —(CH₂)₄— or —CH═CH—CH═CH—, and
q denotes 0 or 1, or
where Y denotes a heterocyclic radical (b),
R⁵ denotes H or CN,
R⁶ denotes H, $CH_3$ or $C_2H_5$,
R⁷ denotes H or $CF_3$, and
R⁸ denotes $C_5$-$C_6$-cycloalkyl, phenyl, or phenyl which is substituted by Cl or $OCH_3$, or, if R⁵ denotes CN and/or R⁷ denotes $CF_3$, additionally denotes H, or
where Y denotes a heterocyclic radical (c),
R⁹ denotes H,
R¹⁰ denotes CN, $COOCH_3$ or $COOC_2H_5$,
R¹¹ denotes $CH_3$, $C_2H_5$, $OCH_3$, $OC_2H_5$, F, Cl, Br or $CF_3$, and
n denotes 0, 1 or 2, where, if R¹¹ denotes $CF_3$, n is 1 and, if n does not equal 0, R¹¹ may be in the 5, 6, 7 or 8 position, or
where Y denotes the heterocyclic radical (d),
R¹³ denotes a phenyl group which is unsubstituted or substituted by 1 or 2 F, Cl, $OCH_3$ or $CH_3$.

The compounds of the formula IIIa in which R¹, g and Y have the specified meanings are new and represent valuable intermediates for the preparation of the compounds of the formula I, which have a strong antimycotic and fungicidal action. Some of the compounds of the formula IIIa likewise have an antimycotic or fungicidal action. Some of the compounds of the formula IIIa additionally exhibit pharmacological actions, such as, for example, actions on the cardiovascular system, inter alia by favorably influencing the blood pressure.

In addition, the invention relates to a process for the preparation of compounds of the formula IIIa, wherein a compound of the formula XIII,

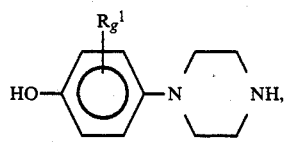

in which R¹ and g have the meanings specified in the case of formula I, or a salt of this compound, is reacted with a compound of the formula X, $$E''-Y \quad\quad X,$$

in which

E'' denotes $C_1-C_4$-alkoxy, Cl, Br, I, acyloxy, such as acetoxy or benzoyloxy, alkylsulfonyloxy, such as methanesulfonyloxy, or arylsulfonyloxy, such as benzene-, nitrobenzene- or toluenesulfonyloxy, and Y has the meanings specified in the case of formula I, and, if appropriate, the compounds of the formula IIIa obtained are converted into their acid-addition salts using inorganic or organic acids.

For the reaction according to the invention with compounds of the formmula XIII, any of (a) a compound of the formula $Xa_1$ or of the formula $Xa_2$,

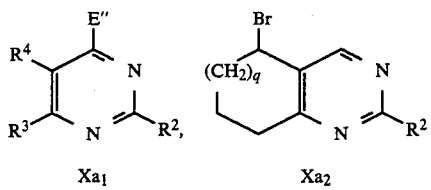

in which $R^2-R^4$ and q have the meanings specified in the case of the formula I, and E'' denotes Cl, Br or $OCH_3$, or (b) a compound of the formula Xb,

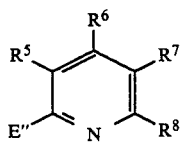

in which $R^5-R^8$ have the meanings specified in the case of the formula I, and E'' denotes Cl,

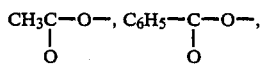

$CH_3-SO_2-O-$, $\quad 4-CH_3-C_6H_4-SO_2-O-$ or $C_6H_5-SO_2-O-$, or (c) a compound of the formula Xc,

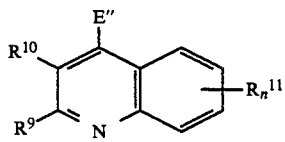

in which $R^9-R^{11}$ and n have the meanings specified in the case of the formula I, and E'' denotes Cl or Br, or (d) a compound of the formula Xd,

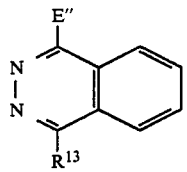

in which $R^{13}$ has the meanings specified in the case of the formula I, and E'' denotes Cl, is preferably used.

Particularly preferred compounds of the formulae $Xa_1$, Xb, Xc and Xd for the reaction with a compound of the formula XIII are those in which E'' denotes Cl.

The process, according to the invention, for the preparation of compounds of the formula IIIa is expediently carried out in an inert organic solvent in a temperature range from 20° to 180° C., preferably from 50° to 120° C., advantageously in the presence of a base, which is preferably used in an equivalent amount. If salts of the compounds of the formula XIII are used for the process, the stoichiometric amount of base corresponding to the amount of salt is added. If desired, a further proportion of base can then be used in addition. The synthesis of compounds of the formula IIIa from the compounds of the formulae XIII and X can also be carried out without the addition of base if the compounds XIII are not used in the form of the salt. The reactants of the formulae XIII and X can be used in different molar ratios, i.e. in each case either the compounds of the formula XIII or those of the formula X can be used in excess, but equimolar amounts are advantageously used.

Suitable solvents are, for example, hydrocarbons, ethers in general, such as diethyl ether, 1,2-dimethoxyethane, tetrahydrofuran or dioxane, or acetonitrile, butyronitrile, dimethylformamide, dimethylacetamide, acetone, 4-methyl-2-pentanone, methylene chloride, chloroform, dimethyl sulfoxide, anisole, chlorobenzene or tetrachloroethene, or mixtures of these solvents.

Suitable bases are those mentioned as examples in process version (A).

Depending on the temperature range, the reaction times are a few minutes to several hours.

If necessary, the process products can be purified by recrystallization from a suitable solvent or mixture of solvents or by column chromatography on a silica gel.

Preparation of the starting materials:

The compound of the formula XIII where g=0 is known. Compounds of the formula XIII in which g denotes 1 or 2 and R¹ has the meanings specified in the case of the formula I are prepared, analogously to the known compounds, by reaction of appropriate 4-methoxyanilines with bis-(2-chloroethyl)amine and subsequent cleavage of the phenol ether using concentrated aqueous hydrobromic acid. The preparation of the compounds of the formula X in which E'' and Y have the specified meanings, if they are not known, has already been described in process version (D).

The compounds of the formula I and their acid-addition salts are valuable medicaments. They have an antimicrobial action and in particular are suitable for the prevention and treatment of fungal infections in humans and in various species of mammal.

In vitro, the new compounds have a very good action against dermatophytes, such as, for example, *Trichophyton mentagrophytes, Microsporum canis* and *Epidermophyton floccosum;* against mold fungi, such as, for example, *Aspergillus niger,* or against yeasts, such as, for example, Candida albicans, C. tropicalis, Torulopsis glabrata and Trichosporon cutaneum, or against protozoa, such as Trichomonas vaginalis or T. fetus, or against Gram-positive and Gram-negative bacteria.

After oral or parenteral administration, the compounds also have a very good systemic effect in vivo, for example against Candida albicans, for example in experimental kidney candidiasis of the mouse. There is likewise a very good effect against various pathogens of dermatomycosis (for example Trichophyton metagrophytes) in guinea pigs after oral, parenteral or local administration.

The following may be mentioned as examples of areas of indication in human medicine:

Dermatomycosis and systemic mycosis caused by Trichophyton mentagrophytes and other Trichophyton species, Microsporon species, Epidermophyton floccosum, gemmiparous fungi, biphasic fungi and mold fungi.

The following may be mentioned as examples of areas of indication in veterinary medicine:

All dermatomycoses and systemic mycoses, particularly those which are caused by the abovementioned pathogens.

The present invention includes pharmaceutical preparations, which, beside nontoxic, inert pharmaceutically suitable excipients, contain one or more active compounds according to the invention or which comprise one or more active compounds according to the invention, and also processes for the preparation of these preparations. Nontoxic, inert pharmaceutically suitable excipients are taken to mean solid, semisolid or liquid diluents, fillers and formulation auxiliaries of all types.

Suitable forms of administration are, for example, tablets, dragees, capsules, pills, aqueous solutions, suspensions, and emulsions, optionally sterile injectable solutions, nonaqueous emulsions, suspensions and solutions, ointments, creams, pastes, lotions, sprays etc.

The therapeutically active compounds should expediently be present in the abovementioned pharmaceutical preparations in a concentration of about 0.01 to 99.0, preferably of about 0.05 to 50% by weight of the total mixture.

The abovementioned pharmaceutical preparations may also contain further pharmaceutical active compounds in addition to the active compounds according to the invention.

The abovementioned pharmaceutical preparations are prepared in a conventional fashion by known methods, for example by mixing the active compound(s) with the excipient(s).

The present invention also includes the use of the active compounds according to the invention and the use of pharmaceutical preparations which contain one or more active compounds according to the invention in human and veterinary medicine for the prevention, improvement and or cure of the abovementioned disorders.

The active compounds or the pharmaceutical preparations may be administered locally, orally, parenterally, intraperitoneally and/or rectally.

In order to achieve the desired results, it has generally proven expedient, both in human and in veterinary medicine to administer the active compound or compounds according to the invention in total amounts of about 0.05 to about 200, preferably 0.1 to 100, in particular 0.5 to 30 mg/kg of bodyweight per 24 hours, if appropriate in the form of several individual doses. The total amount is administered in 1 to 8, preferably in 1 to 3, individual doses.

However, it may be necessary to deviate from the dosages mentioned, and in particular to do so as a function of the species and the bodyweight of the object to be treated, the nature and severity of the disorder, the type of the preparation and the administration of the medicament, and the period of time or interval over which the administration is effected. Thus, it may in some cases be sufficient to manage with less than the abovementioned amount of active compound, whereas in other cases, it is necessary to exceed the abovementioned amount of active compound. The optimum dosage and the type of administration of the active compounds required in each case can easily be determined by any expert on the basis of his expert knowledge.

The new compounds of the formula I are also suitable for the treatment of protozoosis in humans and animals as is caused, for example, by infection by Trichomonas vaginalis, Entamoeba histolytica, Trypanosoma cruzi and Leishmania donovani.

The new compounds may be administered orally or locally. Oral administration is carried out in pharmaceutically conventional preparations, for example in the form of tablets or capsules.

The compounds of the formula I are also active as biocides. They are distinguished, in particular, by their fungicidal activity in the case of phytopathogenic fungi. Even fungal pathogens which have already penetrated into the vegetative tissue can be combated successfully. This is particularly important and advantageous in those fungal diseases which, once the infection has occurred, can no longer be combated effectively using the fungicides which are otherwise conventional. The range of action of the new compound covers a large number of different phytopathogenic fungi, such as, for example, Piricularia oryzae, Plasmo-para viticola, various types of rust, but above all Venturia inaequalis, Cercospora beticola and powdery mildew fungi in fruit, vegetable, cereal and ornamental plant growing.

The new compounds of the formula I are furthermore suitable for use in industrial areas, for example as wood-protection agents, as preservatives in paints, in cooling lubricants for metal working, or as preservatives in drilling and cutting oils.

The new compounds may be used in the conventional preparations as wettable powders, emulsifiable concentrates sprayable solutions, dusting agents, dressing agents, dispersions, granules or microgranules.

The following examples serve to illustrate the invention in greater detail, without limiting it.

EXAMPLES OF PREPARATION PROCESS VERSION (A)

EXAMPLE 1

A mixture of 1.51 g (3.7 mmol) of 1-(4-hydroxy-3,5-dimethylphenyl)-4-(6-(2-cyclopentylethyl)-2-ethyl-pyrimidin-4-yl)piperazine, 1.51 g (3.7 mmol) of 2-S,(R)-(2,4-dichlorophenyl)-2-(imidazol-1-ylmethyl)-4-R,(S)-methanesulfonyloxymethyl-1,3-dioxolane (cis form), 0.28 g of tetrabutylammonium bromide, 33 ml of toluene and 5.5 ml of 50% strength sodium hydroxide solution was stirred vigorously for 3.5 hours at 100° C. The phases were then separated at room temperature, the concentrated NaOH was extracted by shaking twice with ether, the toluene and ether phases were combined, and these were shaken three times with water.

The toluene/ether solution was dried, filtered and evaporated in vacuo in a rotary evaporator. The residue (3.20 g) was chromatographed on a silica gel S/$CH_2-Cl_2$ column (diameter 2.0 cm, height 33 cm) with elution using $CH_2Cl_2$ and $CH_2Cl_2/C_2H_5OH$ mixtures with increasing $C_2H_5OH$ content (to a maximum of 4% by volume). After elution of preliminary fractions (content 0.25 g), the fractions which were unary according to TLC were combined and evaporated in vacuo. 2.15 g (=81% yield) of 2-S,(R)-(2,4-dichlorophenyl)-2-(imidazol-1-ylmethyl)-4-R,(S)-[(4-(4-(6-(2-cyclopentylethyl)-2-ethylpyrimidin-4-yl)piperazin-1-yl)-2,6-dimethylphenoxy)methyl]-1,3-dioxolane (cis form), pure according to TLC, were obtained as a highly viscous oil; analysis: $C_{39}H_{48}Cl_2N_6O_3$ (MW 719.78) calc. C 65.08, H 6.72, N 11.68; found C 65.0, H 7.1, N 11.5%.

EXAMPLE 2

154 mg (5.13 mmol) of an 80% strength sodium hydride/oil dispersion were added to a solution of 1.803 g (5 mmol) of 1-(4-hydroxyphenyl)-4-(5,6-dimethyl-2-phenyl-pyrimidin-4-yl)piperazine in 20 ml of absolute N,N-dimethylformamide (DMF) at room temperature. When the evolution of hydrogen had subsided, a solution of 2.10 g (5.14 mmol) of 2-S,(R)-(2,4-dichlorophenyl)-2-(1,2,4-triazol-1-ylmethyl)-4-R,(S)-methanesulfonyloxymethyl-1,3-dioxolane (cis form) in 15 ml of absolute DMF was added, and the mixture was stirred for 3 hours at 95°-97° C. The DMF was subsequently removed by distillation in vacuo (3-10 mbar) in a rotary evaporator, 50 ml of water and 50 ml of $CH_2Cl_2$ were added to the residue and the mixture was shaken thoroughly, the phases were separated, and the aqueous phase was extracted three times with with $CH_2Cl_2$. The combined $CH_2Cl_2$ extracts were dried using $MgSO_4$, filtered and evaporated in vacuo. The residue remaining (3.9 g) was chromatographed on a silica gel S/$CH_2Cl_2$ column (diameter 2.0 cm, height 30 cm) with elution using $CH_2Cl_2$ and $CH_2Cl_2/C_2H_5OH$ mixtures, with increasing $C_2H_5OH$ content (to a maximum of 2% by volume). After elution of preliminary fractions (content 0.95 g), the fractions which were unary according to TLC were combined and evaporated in vacuo. 2.31 g (=69% yield) of 2-S,(R)-(2,4-dichlorophenyl)-2-(1,2,4-triazol-1-ylmethyl)-4-R,(S)-[4-(4-(5,6-dimethyl-2-phenylpyrimidin-4-yl)piperazin-1-yl)-phenoxymethyl]-1,3-dioxolane (cis form) were obtained as a highly viscous oil;

analysis: $C_{35}H_{35}Cl_2N_7O_3$ (MW 672.64): calc. C, 62.50; H, 5.25; Cl, 10.54; N, 14.58; found C, 61.8; H, 5.3; Cl, 11.0; N, 14.3%.

EXAMPLE 3

The compounds of the formula I (g=0 or 2, $R^1$=H or $CH_3$ in the 2,6 position) shown in Table 1 were prepared by the same procedure as described in Example 1, starting from IIb or IIc (cf. Table 1) and in each case the appropriate compound IIIa (Y, cf. Table 1).

TABLE 1

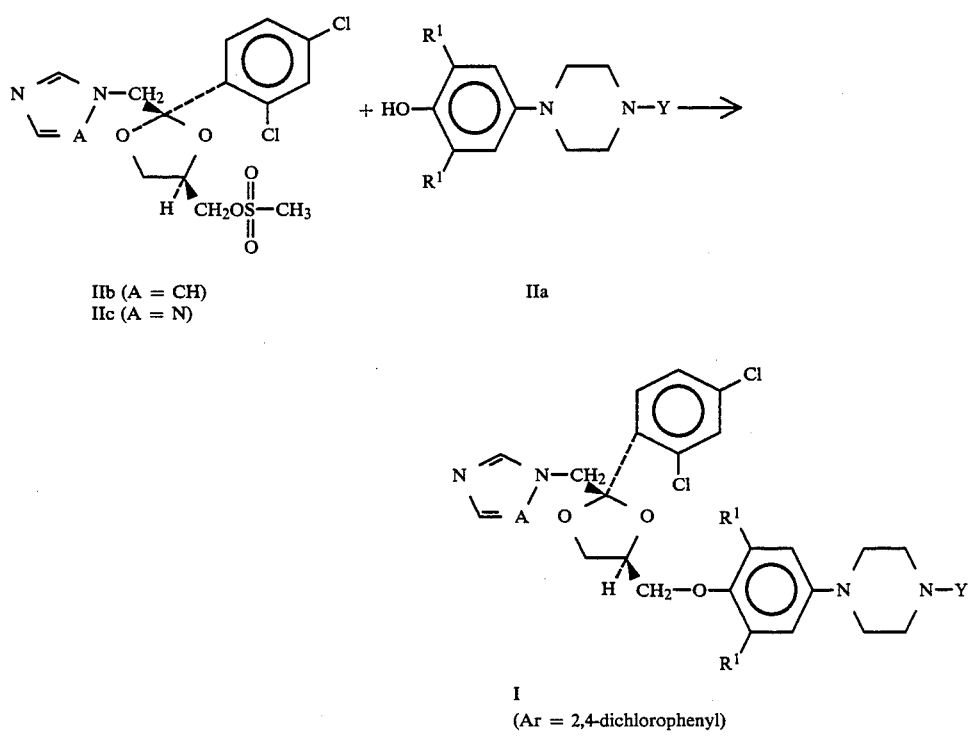

| Comp. No. | A | $R^1$ | Y | Analysis % calc. | found | m.p. [°C.] | 2,4-isomers |
| --- | --- | --- | --- | --- | --- | --- | --- |

TABLE 1-continued

| No. | X | R | Structure | Elem. | Calc. | Found | m.p. | isomer |
|---|---|---|---|---|---|---|---|---|
| 1.1 | CH | H | (pyrimidine with C₂H₅ and cyclopentylethyl substituents) | C<br>H<br>N | 64.25<br>6.41<br>12.15 | 64.7<br>6.6<br>12.0 | — | cis |
| 1.2 | N | CH₃ | (pyrimidine with CH₃, CH₃ and phenyl substituents) | C<br>H<br>Cl<br>N | 63.42<br>5.61<br>10.12<br>13.99 | 62.8<br>5.6<br>10.8<br>13.8 | — | cis |
| 1.3 | N | H | (pyrimidine with benzyl, CH₃ and 4-chlorophenyl substituents) | C<br>H<br>N | 62.88<br>4.89<br>12.52 | 62.9<br>4.8<br>12.6 | 167–68 | cis |
| 1.4 | CH | H | (pyrimidine with C₈H₁₇ and phenyl substituents) | C<br>H<br>N | 66.74<br>6.40<br>11.12 | 65.7<br>6.3<br>10.7 | — | cis |
| 1.5 | CH | H | (tetrahydroquinazoline with phenyl) | C<br>H<br>N | 65.42<br>5.49<br>12.05 | 64.9<br>5.4<br>11.8 | 119–20 | cis |
| 1.6 | CH | H | (tetrahydroquinazoline with phenyl) | C<br>H<br>N | 65.42<br>5.49<br>12.05 | 65.8<br>5.7<br>12.1 | 96–97 | cis |

TABLE 1-continued

| | | | | | | | | | |
|---|---|---|---|---|---|---|---|---|---|
| 1.7 | CH | H | (4-cyano-2-methyl-6-phenylpyridin-3-yl) | | C<br>H<br>N | 65.20<br>5.03<br>12.22 | 65.4<br>5.2<br>12.0 | 127–28 | cis |
| 1.8 | CH | H | (3-cyano-4-methyl-6-chloro-8-methylquinolin-2-yl) | | C<br>H<br>N | 60.92<br>4.53<br>12.18 | 60.4<br>4.7<br>11.6 | 208–09 | cis |

*Cis and trans relate to the azolylmethyl radical and the (substituted) oxymethyl radical in the 2 or 4 position respectively of the dioxolane ring

EXAMPLE 4

The compounds of the formula I (g=0 or 2, $R^1$=H or $CH_3$ in the 2,6 position; cis form) shown in Table 2 were prepared by the same procedure as described in Example 2, starting from IIb or IIc (cf. Table 1) and in each case the appropriate compound IIa (Y, cf. Table 2).

If a crystalline product was produced after removal of the DMF by distillation and after taking up the residue in water, or if the residue from the $CH_2Cl_2$ extract crystallized, these compounds were purified by recrystallization from methanol or acetonitrile. Compounds isolated in this fashion are marked (*). In all other cased, the compounds shown in Table 2 were obtained by column chromatography as described in Example 2.

TABLE 2

IIb or IIc + IIIa →

I
(Ar = 2,4-dichlorophenyl)

| Comp. No. | A | $R^1$ | Y | Analysis % calc. | found | m.p. [°C.] |
|---|---|---|---|---|---|---|
| 2.1 | CH | H | (4-methyl-6-phenylpyrimidin-2-yl) | C 63.93<br>H 5.21<br>N 12.76 | 63.8<br>5.3<br>12.7 | — |

TABLE 2-continued

| | | | Structure | | Analysis | | m.p. |
|---|---|---|---|---|---|---|---|
| 2.2 | CH | H | (ethyl/benzyl substituted pyrimidine with 2-CH₃) | C<br>H<br>N | 65.23<br>5.76<br>12.01 | 65.0<br>5.8<br>11.8 | — |
| 2.3 | CH | H | (4,5-dimethyl-2-(4-chlorophenyl substituent) pyrimidine) | C<br>H<br>N | 61.24<br>5.00<br>11.90 | 60.1<br>5.4<br>11.3 | 150–51 |
| 2.4 | CH | H | (4,5,6-trimethyl-2-phenylpyrimidine) | C<br>H<br>Cl<br>N | 64.38<br>5.40<br>10.56<br>12.51 | 64.2<br>5.6<br>11.1<br>12.3 | 76–77 |
| 2.5 | CH | CH₃ | (4,5,6-trimethyl-2-phenylpyrimidine) | C<br>H<br>Cl<br>N | 65.23<br>5.76<br>10.13<br>12.01 | 65.1<br>5.7<br>10.5<br>11.7 | — |
| 2.6 | CH | H | (4,5,6-trimethyl-2-(4-chlorophenyl)pyrimidine) | C<br>H<br>N | 61.24<br>5.00<br>11.90 | 61.5<br>5.1<br>11.7 | 158–59 |
| 2.7 | CH | H | (cyclopentylmethyl substituted 2-phenylpyrimidine) | C<br>H<br>N | 66.57<br>6.00<br>11.36 | 66.3<br>6.0<br>11.3 | — |
| 2.8 | N | CH₃ | (4,5-dimethyl-2-phenyl triazine) | C<br>H<br>N | 63.42<br>5.61<br>13.99 | 63.1<br>5.7<br>13.6 | — |

TABLE 2-continued

| | | | Structure | | Anal. Calc. | Found | mp (°C) |
|---|---|---|---|---|---|---|---|
| 2.9 | N | H | (cyclohexeno-pyrimidine with phenyl) | C | 63.61 | 63.6 | — |
| | | | | H | 5.34 | 5.3 | |
| | | | | N | 14.03 | 13.9 | |
| 2.10 | CH | H | (cyclohexeno-pyridine with phenyl) | C | 65.42 | 65.1 | 119–20 |
| | | | | H | 5.49 | 5.3 | |
| | | | | Cl | 10.16 | 10.6 | |
| | | | | N | 12.05 | 11.7 | |
| 2.11* | CH | H | (cyclohexeno-pyrimidine with C$_2$H$_5$) | C | 62.87 | 62.0 | 142–43 |
| | | | | H | 5.89 | 5.9 | |
| | | | | N | 12.94 | 13.5 | |
| 2.12 | CH | H | (cyclohexeno-pyrimidine with phenyl) | C | 65.42 | 65.4 | 96–97 |
| | | | | H | 5.49 | 5.3 | |
| | | | | Cl | 10.16 | 10.3 | |
| | | | | N | 12.05 | 11.9 | |
| 2.13 | N | CH$_3$ | (cyclohexadieno-pyrimidine with phenyl) | C | 64.82 | 64.4 | — |
| | | | | H | 5.16 | 5.0 | |
| | | | | N | 13.57 | 13.2 | |
| 2.14 | CH | H | (pyridyl-CF$_3$) | C | 56.79 | 56.3 | — |
| | | | | H | 4.45 | 4.5 | |
| | | | | N | 11.04 | 11.3 | |
| 2.15 | N | H | (pyridyl-CF$_3$) | C | 54.81 | 54.7 | 99–100 |
| | | | | H | 4.28 | 4.4 | |
| | | | | N | 13.23 | 13.1 | |

TABLE 2-continued

| No. | A | R | Structure | Analysis | Calc. | Found | m.p. (°C) |
|---|---|---|---|---|---|---|---|
| 2.16 | CH | CH₃ | 6-methyl-3-(trifluoromethyl)pyridin-2-yl | C<br>H<br>N | 58.01<br>4.87<br>10.57 | 57.5<br>4.9<br>10.4 | — |
| 2.17 | CH | H | 6-methyl-2-phenylpyridin-... | C<br>H<br>N | 65.42<br>5.18<br>10.90 | 66.2<br>5.1<br>10.9 | — |
| 2.18* | CH | H | 3-cyano-4,6-dimethyl-2-phenylpyridin-... | C<br>H<br>N | 65.20<br>5.03<br>12.33 | 65.1<br>5.0<br>12.0 | 127–28 |
| 2.19* | N | H | 3-cyano-4,6-dimethyl-2-phenylpyridin-... | C<br>H<br>N | 63.34<br>4.87<br>14.36 | 63.5<br>4.8<br>14.6 | 117–18 |
| 2.20 | N | H | 4,6-dimethyl-2-phenylpyridin-... | C<br>H<br>N | 63.44<br>5.93<br>12.68 | 63.0<br>5.7<br>12.7 | — |
| 2.21 | CH | H | 3-(ethoxycarbonyl)-4-methyl-8-(trifluoromethyl)quinolin-... | C<br>H<br>N | 58.73<br>4.53<br>9.26 | 58.5<br>4.6<br>9.0 | — |
| 2.22 | CH | H | 3-(ethoxycarbonyl)-4-methyl-8-(trifluoromethyl)quinolin-... | C<br>H<br>N | 57.07<br>4.39<br>11.09 | 56.1<br>4.3<br>10.9 | — |
| 2.23 | CH | H | 3-(ethoxycarbonyl)-4-methyl-7-ethoxyquinolin-... | C<br>H<br>N | 62.29<br>5.37<br>9.56 | 62.0<br>5.2<br>9.2 | 118–19 |

TABLE 2-continued

| | | | | | | calc. | found | |
|---|---|---|---|---|---|---|---|---|
| 2.24* | CH | H | (structure: N—N linked ring with CH₃ phenyl and cyclohexadiene) | | C<br>H<br>N | 66.19<br>5.13<br>11.88 | 65.0<br>5.0<br>10.9 | 254–55 |
| 2.25* | N | H | (structure: N—N linked ring with CH₃ phenyl and cyclohexadiene) | | C<br>H<br>N | 64.40<br>4.98<br>13.84 | 63.7<br>5.0<br>13.7 | 246–47 |

EXAMPLE 5

0.58 g (5.15 mmol) of potassium tert.-butylate was added to a solution of 1.62 g (5 mmol) of 1-(4-hydroxyphenyl)-4-(5-trifluoromethylpyrid-2-yl)piperazine in 20 ml of absolute DMF at room temperature, the mixture was stirred for 10 minutes, a solution of 2.04 g (5 mmol) of IIb (cf. Example 3, Table 1) in 15 ml of absolute 1,2-dimethoxyethane (DME) was then added, and the mixture was stirred for 5.5 hours at 92°–93° C. The solvents were subsequently stripped off in vacuo, the residue was taken up in water/CH$_2$Cl$_2$, and the phases were separated after shaking thoroughly. The aqueous phase was extracted a further twice with CH$_2$Cl$_2$. The combined CH$_2$Cl$_2$ extracts were dried, filtered and evaporated in vacuo. The residue remaining (3.4 g) was chromatographed on a silica gel/CH$_2$Cl$_2$ column (diameter 2.1 cm, height 30 cm) by elution with CH$_2$Cl$_2$ and CH$_2$Cl$_2$/C$_2$H$_5$OH mixtures (C$_2$H$_5$OH content: 0.1–2.0% by volume). After combining and evaporating the fractions which were unary according to TLC, 2.0 g (=63% yield) of cis-2-(2,4-dichlorophenyl)-2-(imidazol-1-ylmethyl)-4-[4-(4-(5-trifluoromethylpyrid-2-yl)piperazin-1-yl)phenoxymethyl]-1,3-dioxolane were obtained as a highly viscous oil.

EXAMPLE 6

By the same procedure as described in Example 5, likewise on a 5 mmol scale, using the same piperazine derivative as intermediate and using IIb (cf. Example 3, Table 1) and using 0.207 g (5.3 mmol) of sodium amide as base in place of potassium tert.-butylate, otherwise under the same reaction conditions and using the same work-up as described in Example 5, 2.11 g (=66.6% yield) of cis-2-(2,4-dichlorophenyl)-2-(imidazol-1-ylmethyl)-4-[4-(4-(5-trifluoromethylpyrid-2-yl)piperazin-1-yl)phenoxymethyl]-1,3-dioxolane were obtained.

EXAMPLE 7 (salt formation)

0.585 ml of a 6M solution of HCl in ether was added to a solution of 1.11 g (1.75 mmol) of 2-S,(R)-(2,4-dichlorophenyl)-2-(imidazol-1-ylmethyl)-4-R,(S)-[4-(4-(5-trifluoromethylpyrid-2-yl)-piperazin-1-yl)phenoxymethyl]-1,3-dioxolane (cis form) (cf. Examples 5 and 6) in 15 ml of ethyl acetate, whereupon a crystalline precipitate was produced.

The mixture was evaporated in vacuo, and the crystalline residue remaining was boiled for 8 minutes in 25 ml of acetone and, after cooling to <9° C., filtered off under suction and dried. 1.22 g (=98.5% yield of the dihydrochloride) of cis-2-(2,4-dichlorophenyl)-2-(imidazol-1-ylmethyl)-4-[4-(4-(5-trifluoromethylpyrid-2-yl)piperazin-1-yl)phenoxy-methyl]-1,3-dioxolane dihydrochloride wre obtained;

melting point 205°–06° C.;

analysis: C$_{30}$H$_{30}$Cl$_4$F$_3$N$_5$O$_3$ (MW 707.44), calc. C, 50.93; H, 4.27; Cl$^-$, 10.02; N, 9.90; found C, 51.7; H, 4.3; Cl$^-$, 7.9; N, 9.9%.

EXAMPLES OF PREPARATION PROCESS VERSION (B)

EXAMPLE 8

(a) 0.367 g (12.24 mmol) of an 80% strength sodium hydride/oil dispersion was added (with cooling) to a solution of 4.64 g (12 mmol) of 1-(4-hydroxyphenyl)-4-(5,6,7,8-tetrahydro-2-phenylquinazolin-4-yl)piperazine in 48 ml of absolute DMF at room temperature. When the evolution of hydrogen was complete, a solution of 4.43 g (12 mmol) of cis-2-bromomethyl-2-(4-fluorophenyl)-4-methanesulfonyloxymethyl-1,3-dioxolane (cis and trans relate to the bromomethyl and methanesulfonyloxymethyl groups in the 2 and 4 positions respectively of the dioxolane ring) in 35 ml of absolute DMF was added dropwise at room temperature, and the mixture was stirred for 4 hours at 100° C. The DMF was subsequently evaporated in vacuo, the residue was taken up in ether/water, the phases were separated after vigorous mixing, and the aqueous phase was extracted by shaking a further three times with ether. The ether extracts were combined, dried and evaporated in vacuo. The residue remaining (8.0 g) was chromatographed on a silica gel S/CH$_2$Cl$_2$/petroleum ether 1:1 column (diameter 3.0 cm, height 41 cm) with elution using CH$_2$Cl$_2$/petroleum ether mixtures with increasing CH$_2$Cl$_2$ content (to a maximum of 75% by volume of CH$_2$Cl$_2$). After elution of preliminary fractions (content about 1 g), the fractions which were virtually unary according to TLC were combined, evaporated and crystallized from ether. In this fashion, 6.0 g (=76% yield) of pure cis-2-bromomethyl-2-(4-fluorophenyl)-4-[4-(4-(5,6,7,8-tetrahydro-2-phenylquinazolin-4-yl)piperazin-1-yl)phenoxymethyl]-1,3-dioxolane, melting point 170°–71° C., were obtained;

analysis: C$_{35}$H$_{36}$BrFN$_4$O$_3$ (MW 659.62); calc. C, 63.73; H, 5.50; Br, 12.12; N, 8.49; found C, 63.4; H, 5.5; Br, 12.6; N, 8.4%.

(b) 0.54 g (18 mmol) of an 80% strength sodium hydride/oil dispersion was added to a solution of 1.23 g (18.1 mmol) of imidazole in 25 ml of absolute dimethyl solfoxide at room temperature, and the mixture was stirred for 30 minutes at room temperature. 5.94 g (9.2 mmol) of cis-2-bromomethyl-2-(4-fluorophenyl)-4-[4-(4-(5,6,7,8-tetrahydro-2-phenylquinazolin-4-yl)piperazin-1-yl)phenoxymethyl]-1,3-dioxolane (prepared under (a)) were subsequently added, and the mixture was stirred for 30 hours at 130° C. under a nitrogen atmosphere. The dimethyl sulfoxide (DMSO) was removed by distillation in an oil-pump vacuum in a rotary evaporator. The residue remaining was taken up in $CH_2Cl_2$/water. After thorough mixing and separating the phases, the aqueous solution was extracted three times with $CH_2Cl_2$. The combined $CH_2Cl_2$ extracts were evaporated in vacuo. The residue remaining (6.5 g) was chromatographed on a silica gel S/$CH_2Cl_2$/petroleum ether 1:1 column (diameter 2.6 cm, height 40 cm) with elution using $CH_2Cl_2$/petroleum ether 1:1; 2:1–4:1; $CH_2Cl_2$ and $CH_2Cl_2$/$C_2H_5OH$ mixtures with increasing $C_2H_5OH$ content (to a maximum of 1.6% by volume of $C_2H_5OH$). After combining and evaporating the fractions which were unary according to TLC, 1.67 g (=28.7% yield) of pure cis-2-(4-fluorophenyl)-2-(imidazol-1-ylmethyl)-4-[4-(4-(5,6,7,8-tetrahydro-2-phenylquinazolin-4-yl)piperazin-1-yl)phenoxymethyl]-1,3-dioxolane, melting point 161°–62° C., were obtained;

analysis: $C_{38}H_{39}FN_6O_3$ (MW 646.78); calc. C, 70.57; H, 6.08; F, 2.94; N, 12.99; found C, 69.9; H, 6.0; F, 2.7; N, 12.8%.

EXAMPLE 9

(a) A mixture of 3.605 g (10 mmol) of 1-(4-hydroxyphenyl)-4-(2-methyl-4-(4-tolyl)pyrimidin-6-yl)piperazine, 80 ml of toluene, 4.20 g (10 mmol) of 2-bromomethyl-2-(2,4-dichlorophenyl)-4-methanesulfonyloxymethyl-1,3-dioxolane (cis/trans mixture), 0.65 g of tetrabutylammonium bromide and 13.5 ml of 50% strength sodium hydroxide solution was stirred vigorously for 4 hours at 55° C. The phases were subsequently separated at room temperature, the sodium hydroxide solution was extracted by shaking three times with ether, and the tolune and ther phases were combined. These were washed three times with water, dried, filtered and evaporated in vacuo. The residue remaining (7.4 g) was chromatographed on a silica gel S/$CH_2Cl_2$ column (diameter 2.6 cm, height 11 cm) with elution using $CH_2Cl_2$. After elution, the fractions which were unary according to TLC were combined and evaporated in vacuo. 6.27 g (=91.6% yield) of 2-bromomethyl-2-(2,4-dichlorophenyl)-4-[4-(4-(2-methyl-4-(4-tolyl)pyrimidin-6-yl)piperazin-1-yl)phenoxymethyl]-1,3-dioxolane (cis/trans mixture) were obtained as a highly viscous oil;

analysis: $C_{33}H_{33}BrCl_2N_4O_3$ (MW 684.49) calc. C, 57.91; H, 4,86; Br, 11.68; Cl, 10.36; N, 8.19; found C, 57.8; H, 4.8; Br, 11.8; Cl, 10.5; N, 8.0%.

(b) 6.21 g (9.1 mmol) of 2-bromomethyl-2-(2,4-dichlorophenyl)-4-[4-(4-(2-methyl-4-(4-tolyl)pyrimidin-6-yl)piperazin-1-yl)phenoxymethyl]-1,3-dioxolane (mixture of cis/trans diastereomers) were reacted with 1.244 g (18.3 mmol) of imidazole and 0.55 g (18.2 mmol) of an 80% strength sodium hydride/oil dispersion in 26 ml of absolute dimethyl sulfoxide as described in Example 8b. After stirring for 26 hours at 130° C., the dimethyl sulfoxide (DMSO) was removed by distillation in an oil-pump vacuum. The residue remaining was taken up in $CH_2Cl_2$/water. After thorough mixing and subsequent separation of the phases, the aqueous solution was extracted three times with $CH_2Cl_2$. The combined $CH_2Cl_2$ extracts were evaporated in vacuo. The residue remaining ( 4.30 g) was chromatographed on a silica gel S/$CH_2Cl_2$ column (diamter 2.0 cm, height 20 cm) with elution using $CH_2Cl_2$ and $CH_2Cl_2$/$C_2H_5OH$ mixtures (0.5–3.0% by volume of $C_2H_5OH$). The fractions containing the diastereomer racemates (check using TLC) were combined and evaporated in vacuo. In this fashion, 3.12 g (=51% yield) of 2-(2,4-dichlorophenyl)-2-(imidazol-1-ylmethyl)-4-[4-(4-(2-methyl-4-(4-tolyl)-pyrimidin-6-yl)piperazin-1-yl)phenoxymethyl]-1,3-dioxolane (mixture of cis/trans diastereomers) were obtained as a viscous oil;

analysis: $C_{36}H_{36}Cl_2N_6O_3$ (MW 671.65) calc. C, 64.38; H, 5.40; N, 12.51; found C, 62.8; H, 5.6; N, 11.8%.

EXAMPLE 10

Using the same procedure as described in Example 8a, starting from 20 mmol of 1-(4-hydroxyphenyl)-4-(5-trifluoromethylpyrid-2-yl)piperazine, the appropriate amount of NaH, and 20 mmol of 2-bromomethyl-2-(2,4-dichlorophenyl)-4-methanesulfonyloxymethyl-1,3-dioxolane (cis/trans mixture), 8.92 g (=69% of theory) of 2-bromomethyl-2-(2,4-dichlorophenyl)-4-[4-(4-(5-trifluoromethylpyrid-2-yl)piperazin-1-yl)phenoxymethyl]-1,3-dioxolane (cis/trans mixture) were obtained as a highly viscous oil;

analysis: $C_{27}H_{25}BrCl_2F_3O_3$ (MW 647.35) calc. C, 50.10; H, 3.89; F, 8.81; N, 6.49; found C, 49.2; H, 3.7; F, 8.2; N, 6.6%.

EXAMPLE 11

A solution of 1.03 g (14.9 mmol) of 1,2,4-triazole in 7 ml of absolute dimethyl sulfoxide (DMSO) was added dropwise to a suspension of 0.49 g (16.3 mmol) of an 80% strength NaH/oil dispersion in 15 ml of absolute DMSO at room temperature, the mixture was stirred for a further 30 minutes at room temperature, and a solution of 6.475 g (10 mmol) of 2-bromomethyl-2-(2,4-dichlorophenyl)-4-[4-(4-(5-trifluoromethylpyrid-2-yl)piperazin-1-yl)phenoxymethyl]-1,3-dioxolane, (cis/trans mixture), prepared according to Example 10, in 7 ml of absolute DMSO was subsequently added, and the mixture was stirred for 28 hours at 130° C. under a nitrogen atmosphere. After cooling, the reaction mixture was stirred into 140 ml of water, and the resultant mixture was extracted repeatedly with $CH_2Cl_2$. The combined $CH_2Cl_2$ extracts were dried, filtered and evaporated in vacuo. The residue (7.0 g) was purified as described in Example 9b by chromatography on a silica gel S/$CH_2Cl_2$ column (diameter 2.6 cm, height 40.0 cm). 1.72 g (=27.0% yield) of virtually pure 2-(2,4-dichlorophenyl)-2-(1,2,4-triazol-1-ylmethyl)-4-([4-(4-(5-trifluoromethylpyrid-2-yl)piperazin-1-yl)phenoxymethyl]-1,3-dioxolane (mixture of cis/trans diastereomers) were obtained as a highly viscous oil from the fractions which were identical according to TLC;

analysis: $C_{29}H_{27}Cl_2F_3N_6O_3$ (MW 635.50), calc. C, 54.81; H, 4.28; F, 8.97; N, 13.23; found C, 54.1; H, 4.4; F, 8.2; N, 12.8%.

EXAMPLES OF PREPARATION PROCESS VERSION (D)

EXAMPLE 12

A solution of 3.67 g (7.5 mmol) of 2-S,(R)-(2,4-dichlorophenyl)-2-(imidazol-1-ylmethyl)-4-R,(S)-(4-piperazinophenoxymethyl)-1,3-dioxolane (cis form) and 1.40 g (7.7 mmol) of 2-chloro-5-trifluoromethylpyridine in 30 ml of absolute DMF was warmed to 80° C. under a nitrogen atmosphere, and 173 mg of powdered potassium carbonate were added, with stirring, after 10 minutes. A further 173 mg of powdered $K_2CO_3$ were added after a further 25 minutes, and a 3rd portion of 173 mg of powdered $K_2CO_3$ was added after a further 60 minutes (a total of 519 mg (3.75 mmol) of $K_2CO_3$). The mixture was subsequently stirred for a further 9 hours at 80° C., the DMF was removed by distillation in an oil-pump vacuum in a rotary evaporator, and the residue was taken up in water/$CH_2Cl_2$. After thorough mixing and separating the phases, the aqueous solution was extracted three times with $CH_2Cl_2$. The combined $CH_2Cl_2$ extracts were dried, filtered and evaporated in vacuo. The residue was purified by column chromatography on silica gel S/$CH_2Cl_2$ (diameter 2.6 cm, height 29 cm) with elution using $CH_2Cl_2$ and $CH_2Cl_2$/$C_2H_5OH$ mixtures with increasing $C_2H_5OH$ content (to a maximum of 4% by volume of $C_2H_5OH$). 2.47 g (=52% yield) of pure cis-2-(2,4-dichlorophenyl)-2-(imidazol-1-ylmethyl)-4-[4-(4-(5-trifluoromethylpyrid-2-yl)piperazin-1-yl)phenoxymethyl]-1,3-dioxolane were obtained as a viscous oil;

analysis: $C_{30}H_{28}Cl_2F_3N_5O_3$, calc. C, 56.79; H, 4.45; N, 11.04; found C, 56.4; H, 4.3; N, 11.0%.

EXAMPLE 13

The compounds of the formula I shown in Table 3 were prepared by process version (D) by the same procedure as described in Example 12, starting from IXa or IXb (cf. Table 3) and in each case the appropriate compound of the formula Xa. The addition of $K_2CO_3$ and the subsequent stirring (5–7 hours) were carried out at 90° C. when 4-chloro-pyrimidines were used, and these measures were carried out at 80° C. (subsequent stirring time 4–5 hours) when 4-chloroquinolines were used.

TABLE 3

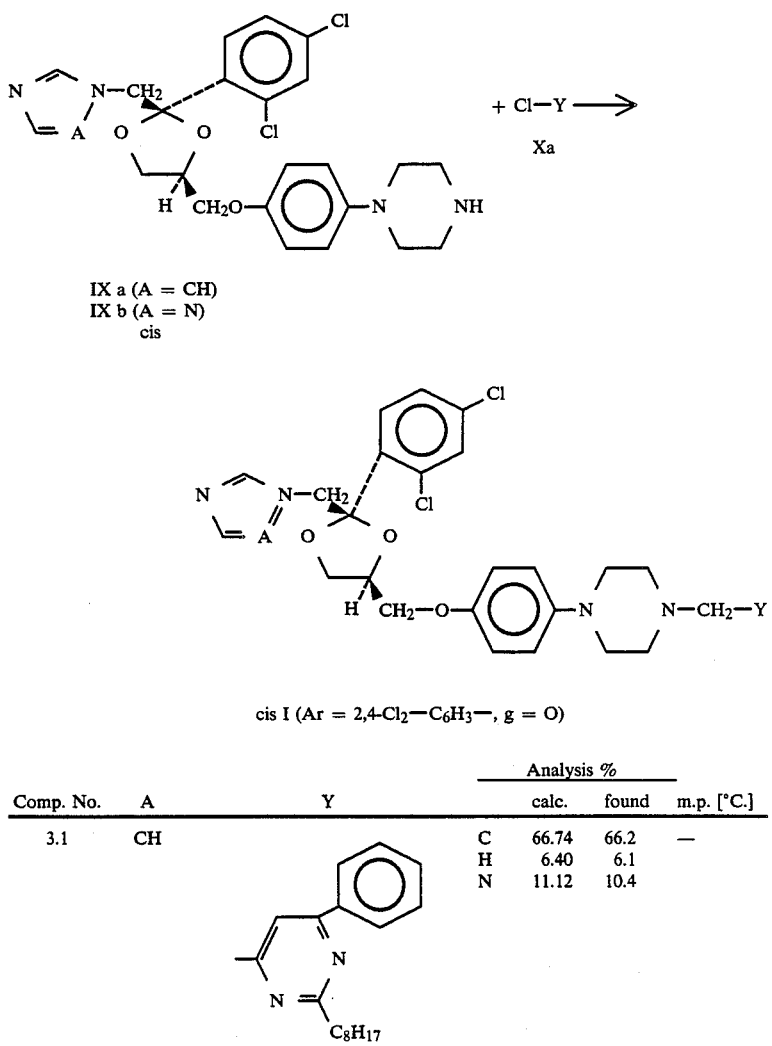

IX a (A = CH)
IX b (A = N)
cis cis I (Ar = 2,4-$Cl_2$—$C_6H_3$—, g = O)

| Comp. No. | A | Y | Analysis % calc. | found | m.p. [°C.] |
|---|---|---|---|---|---|
| 3.1 | CH | (phenyl-pyrimidine-$C_8H_{17}$) | C 66.74<br>H 6.40<br>N 11.12 | 66.2<br>6.1<br>10.4 | — |

TABLE 3-continued

| | | | | | | |
|---|---|---|---|---|---|---|
| 3.2 | N | (structure) | C<br>H<br>N | 62.50<br>5.25<br>14.58 | 62.1<br>5.2<br>14.3 | 122–23 |
| 3.3 | N | (structure) | C<br>H<br>N | 62.50<br>5.25<br>14.58 | 62.0<br>5.1<br>14.2 | — |
| 3.4 | CH | (structure) | C<br>H<br>N | 65.42<br>5.49<br>12.05 | 65.0<br>5.2<br>12.2 | 119–20 |
| 3.5 | CH | (structure) | C<br>H<br>N | 65.42<br>5.49<br>12.05 | —<br>—<br>— | 96–97 |
| 3.6 | CH | (structure) | C<br>H<br>N | 61.24<br>5.00<br>11.90 | 60.9<br>4.9<br>11.6 | 151–52 |
| 3.7 | N | (structure) | C<br>H<br>N | 66.34<br>4.87<br>14.36 | 63.2<br>4.8<br>14.2 | 117–18 |

TABLE 3-continued

| 3.8 | CH | CN (structure) | C | 60.92 | 60.1 | 207–09 |
|-----|----|----|---|-------|------|--------|
|     |    |    | H | 4.53  | 4.2  |        |
|     |    |    | N | 12.18 | 11.8 |        |

Structure: quinoline bearing CN, CH₃ and Cl substituents.

EXAMPLE 14

A mixture of 3.42 g (7 mmol) of cis-2-(2,4-dichlorophenyl)-2-(imidazol-1-ylmethyl)-4-(4-piperazinophenoxymethyl)-1,3-dioxolane, 1.69 g (7 mmol) of 4-chloro-2-phenylquinazoline, 0.45 g of tetrabutylammonium bromide, 55 ml of toluene and 9 ml of 50% strength sodium hydroxide solution was stirred vigorously for 5 hours at 70° C. The phases were then separated at room temperature, the concentrated NaOH was extracted twice by shaking with ether, the toluene and ether phases were combined, and these were shaken three times with water. The toluene/ether solution was dried, filtered and evaporated in vacuo. The residue remaining (4.95 g) was chromatographed as described in Example 1 on a silica gel S/CH$_2$Cl$_2$ column (diameter 2.6 cm, height 30 cm). After combining and evaporating the fractions which were unary according to TLC, 2.49 g (=52% yield) of cis-2-(2,4-dichlorophenyl)-2-(imidazol-1-ylmethyl)-4-[4-(4-(2-phenylquinazolin-4-yl)piperazin-1-yl)phenoxymethyl]-1,3-dioxolane were obtained as a highly viscous oil;

analysis: C$_{38}$H$_{34}$Cl$_2$N$_6$O$_3$ (MW 693.65), calc. C, 65.80; H, 4.94; Cl, 10.22; N, 12.12; found C, 64.8; H, 4.8; Cl, 10.6; N, 11.8%.

EXAMPLES FOR THE PREPARTION OF COMPOUNDS OF THE FORMULA IIIa

EXAMPLE 15

A solution of 1.89 (10.6 mmol) of 1-(4-hydroxyphenyl)piperazine and 2.19 g (10 mmol) of 4-chloro-5,6-dimethyl-2-phenylpyrimidine in 30 ml of absolute N,N-dimethylformamide (DMF) was warmed to 80° C., and 234 mg of powdered K$_2$CO$_3$ were added at 80° C., with stirring, under a nitrogen atmosphere in each case after 10 minutes, after a further 25 minutes and after a further 60 minutes (total addition of 702 mg (5.08 mmol) of K$_2$CO$_3$). The mixture was stirred for a further 6 hours at 90° C., the DMF was substantially removed by distillation in an oil-pump vacuum in a rotary evaporator, the residue remaining was taken up in CH$_2$Cl$_2$/water, and the pH was adjusted to 7–8 using dilute hydrochloric acid. After thoroughly mixing and separating the phases, the aqueous phase was extracted a further twice with CH$_2$Cl$_2$. The combined CH$_2$Cl$_2$ extracts were dried, filtered and evaporated in vacuo. The crystalline residue (3.6 g) was chromatographed on a silica gel S/CH$_2$Cl$_2$ column (diameter 2.0 cm, height 38 cm) by elution with CH$_2$Cl$_2$ and CH$_2$Cl$_2$/C$_2$H$_5$OH mixtures with increasing C$_2$H$_5$OH content (to a maximum of 10% by volume of C$_2$H$_5$OH). The substance was drawn onto the column using 60 ml of a CH$_2$Cl$_2$/tetrahydrofuran 2:1 mixture. The eluted, not completely pure, crystalline substance was purified by boiling with a little CH$_2$Cl$_2$ and filtering off under suction. 2.22 g (=61.5% yield) of pure 1-(4-hydroxyphenyl)-4-(5,6-dimethyl-2-phenylpyrimidin-4-yl)piperazine, melting point 202°–03° C., were obtained;

analysis: C$_{22}$H$_{24}$N$_4$O (MW 360.47), calc.: C, 73.31; H, 6.71; N, 15.54; found: C, 73.2; H, 6.6; N, 15.6%.

EXAMPLE 16

A mixture of 4.42 g (12 mmol) of 1-(4-hydroxy-3,5-dimethylphenyl)piperazine dihydrobromide, 2.84 g (13 mmole) of 4-chloro-5,6-dimethyl-2-phenylpyrimidine, 1.66 g (12 mmol) of powdered K$_2$CO$_3$ and 38 ml of absolute DMF was warmed to 90° C., and 277 mg of powdered K$_2$CO$_3$ were added at 90° C. with stirring in each case after 10 minutes, after a further 25 minutes and after a further 60 minutes (in total 6 mmol of K$_2$CO$_3$), and the mixture was stirred for a further 6 hours at 95° C. The DMF was subsequently removed by distillation in vacuo, the residue was taken up in CH$_2$Cl$_2$/water, the phases were separated after through mixing, and the aqueous phase was extracted a further three times with CH$_2$Cl$_2$. The combined CH$_2$Cl$_2$ extracts were dried, filtered and evaporated in vacuo. The crystalline residue (5.2 g) was boiled with 15 ml of methanol, and the crystals were filtered off under suction after cooling in an ice bath. In this fashion, 3.54 g (=76% yield) of pure 1-(4-hydroxy-3,5-dimethylphenyl)-4-(5,6-dimethyl-2-phenylpyrimidin-4-yl)piperazine, melting point 188°–89° C., were obtained;

analysis C$_{24}$H$_{28}$N$_4$O (MW 388.52) calc. C, 74.20; H, 7.26; N, 14.4; found C, 74.0; H, 7.3; N, 14.3%.

EXAMPLE 17

The compounds of the formula IIIa shown in Table 4 were prepared according to the procedure described in Examples 15 and 16, starting from a compound of the formula XIIIa and in each case the appropriate 4-chloropyrimidine of the formula Xa (cf. Table 4). If the residue remaining after removal of the DMF by distillation was crystalline or crystallized on taking up in water and could be purified by recrystallization (preferably from methanol or acetonitrile), the compound of the formula IIIa concerned was prepared in pure form in this fashion. Otherwise, the compounds IIIa were obtained in pure form by column chromatography according to the procedure described in Example 15. These cases are marked with (*) in Table 4.

TABLE 4

XIIIa + Xa → IIIa (piperazine coupling scheme with HO-aryl-N-piperazine-NH + Cl-Y → HO-aryl-N-piperazine-N-Y)

| Comp. No. | R¹ | Y | Yield [%] | m.p. [°C.] | Empirical formula | Analysis % calc. | found |
|---|---|---|---|---|---|---|---|
| 4.1 | H | 6-methyl-2-ethyl-4-(2-cyclopentylethyl)pyrimidine | 67 | 187–88 | $C_{23}H_{32}N_4O$ | C 72.60<br>H 8.47<br>N 14.72 | 72.5<br>8.4<br>14.5 |
| 4.2* | $CH_3$ | 6-methyl-2-ethyl-4-(2-cyclopentylethyl)pyrimidine | 85 | 134–35 | $C_{25}H_{36}N_4O$ | C 73.49<br>H 8.88<br>N 13.71 | 73.2<br>9.2<br>13.5 |
| 4.3 | H | 4-methyl-6-$C_8H_{17}$-2-phenylpyrimidine | 58 | 121–22 | $C_{28}H_{36}N_4O$ | C 75.64<br>H 8.16<br>N 12.60 | 75.3<br>8.0<br>12.7 |
| 4.4 | H | 4-methyl-6-(2-cyclopentylethyl)-2-phenylpyrimidine | 61 | 147–48 | $C_{27}H_{32}N_4O$ | C 75.67<br>H 7.53<br>N 13.07 | 75.6<br>7.6<br>12.9 |
| 4.5 | H | 4,6-dimethyl-5-methyl-2-(4-chlorophenyl)pyrimidine | 50 | 205–06 | $C_{22}H_{23}ClN_4O$ | C 66.91<br>H 5.87<br>N 14.19 | 66.8<br>5.8<br>14.0 |
| 4.6 | H | 4-methyl-2-phenyl-5,6,7,8-tetrahydroquinazoline | 82 | 227–28 | $C_{24}H_{26}N_4O$ | C 74.58<br>H 6.78<br>N 14.50 | 74.3<br>6.8<br>14.4 |

TABLE 4-continued $$\text{XIIIa} + Cl-Y \longrightarrow \text{IIIa}$$

| Comp. No. | R[1] | Y | Yield [%] | m.p. [°C.] | Empirical formula | Analysis % calc. | found |
|---|---|---|---|---|---|---|---|
| 4.7 | | (cyclohexane-fused pyrimidine with C₂H₅) | 82 | 187–88 | $C_{20}H_{26}N_4O$ | C 70.97<br>H 7.74<br>N 16.55 | 70.7<br>7.8<br>16.4 |
| 4.8 | H | (4-methylphenyl pyrimidine with CH₃) | 89 | 232–33 | $C_{22}H_{24}N_4O$ | C 73.31<br>H 6.71<br>N 15.54 | 73.2<br>6.7<br>15.4 |
| 4.9 | H | (4-chlorophenyl dimethyl pyrimidine) | 87 | 252–53 | $C_{22}H_{23}ClN_4O$ | C 66.91<br>H 5.87<br>N 14.19 | 66.7<br>5.8<br>14.1 |
| 4.10* | H | (benzyl ethyl methyl pyrimidine) | 38 | 148–49 | $C_{24}H_{28}N_4O$ | C 74.20<br>H 7.26<br>N 14.42 | 73.2<br>7.0<br>14.0 |
| 4.11* | $CH_3$ | (benzyl ethyl methyl pyrimidine) | 42 | — | $C_{26}H_{32}N_4O$ | C 74.96<br>H 7.74<br>N 13.45 | 74.6<br>7.6<br>13.4 |
| 4.12* | H | (benzyl methyl 4-chlorophenyl pyrimidine) | 64 | 171–72 | $C_{28}H_{27}ClN_4O$ | C 71.40<br>H 5.78<br>N 11.90 | 71.1<br>5.7<br>11.6 |

TABLE 4-continued $$\text{R}^1\text{-C}_6\text{H}_2(\text{OH})\text{-N(piperazine)NH} + \text{Cl-Y} \longrightarrow \text{R}^1\text{-C}_6\text{H}_2(\text{OH})\text{-N(piperazine)N-Y}$$

XIIIa + Xa → IIIa

| Comp. No. | R¹ | Y | Yield [%] | m.p. [°C.] | Empirical formula | Analysis % calc. | found |
|---|---|---|---|---|---|---|---|
| 4.13 | H | 5-methyl-2-phenyl-5,6,7,8-tetrahydroquinazolin-4-yl | 53 | 240–42 | $C_{24}H_{26}N_4O$ | C 74.58<br>H 6.78<br>N 14.50 | 74.4<br>6.7<br>14.3 |
| 4.14 | H | 4-methyl-2-phenylquinazolin-? | 86 | 191–92 | $C_{24}H_{22}N_4O$ | C 75.37<br>H 5.80<br>N 14.65 | 75.4<br>5.6<br>14.6 |
| 4.15* | H | 3-ethoxycarbonyl-4-methyl-8-trifluoromethylquinolin-? | 72 | 168–69 | $C_{23}H_{22}F_3N_3O_3$ | C 61.99<br>H 4.99<br>N 9.44 | 61.5<br>4.7<br>9.2 |
| 4.16# | H | 3-ethoxycarbonyl-4-methyl-6-ethoxyquinolin-? | 22 | 196–97 | $C_{24}H_{27}N_3O_4$ | C 68.39<br>H 6.46<br>N 9.97 | 67.0<br>6.4<br>10.2 |
| 4.17 | H | 3-cyano-4-methyl-8-methyl-6-chloroquinolin-? | 89 | 226–27 | $C_{21}H_{19}ClN_4O$ | C 66.57<br>H 5.06<br>N 14.79 | 66.5<br>5.1<br>14.5 |

Subsequent stirring time 2.5 hours at 80° C.

EXAMPLE 18

A mixture of 5.11 g (15 mmol) of 1-(4-hydroxyphenyl)piperazine dihydrobromide, 2.48 g (15 mmol) of 1-chlorophthalazine, 2.08 g (15 mmol) of powdered $K_2CO_3$ and 55 ml of absolute DMF was warmed to 85° C., and 346 mg of powdered $K_2CO_3$ were added at 85°

C. with stirring in each case after 10 minutes, after a further 25 minutes and after a further 60 minutes (a total of 1.038 g, 7.51 mmol of $K_2CO_3$), and the mixture was stirred for a further 2 hours at 90° C. and 3 hours at 105° C. The DMF was then removed by distillation in vacuo, the residue was taken up in $CH_2Cl_2$/water, the phases were separated after through mixing, and the aqueous solution was extracted three times with $CH_2Cl_2$. The combined $CH_2Cl_2$ extracts were dried, filtered and evaporated in vacuo. The residue remaining (4.75 g) was chromatographed on a silica gel S/$CH_2Cl_2$ column (diameter 2.6 cm, height 43 cm) by elution with $CH_2Cl_2$/$C_2H_5OH$ mixtures with increasing $C_2H_5OH$ content (1–10% by volume). The fractions in which, according to TLC, the required compound was concentrated were combined and evaporated. The crystalline residue produced (2.04 g) was boiled briefly with 15 ml of $CH_2Cl_2$, cooled in an ice bath, and filtered off under suction. 0.73 g of pure 1-(4-hydroxyphenyl)-4-(1-phthalazinyl)piperazine, melting point 244°–45° C., were thus obtained. The mother liquor was again purified by chromatography in analogous fashion to the first column chromatography on a silica gel/$CH_2Cl_2$ column (diameter 2.0 cm, height 22 cm). The concentrated product produced from this procedure was, like the first part, boiled briefly with 7 ml of $CH_2Cl_2$ and filtered off under suction when cool. A further 0.28 g of pure compound, melting point 244°–45° C., was obtained from this procedure. The total yield was 1.01 g=22% of theory;

analysis: $C_{18}H_{18}N_4O$ (MW 306.37) calc. C, 70.57; H, 5.92; N, 18.29; found C, 69.8; H, 5.9; N, 18.2%.

EXAMPLE 19

35 mmol of 1-(4-hydroxyphenyl)piperazine dihydrobromide, 35 mmol of 1-chloro-4-(4-tolyl)phthalazine and 52.5 mmol of $K_2CO_3$ in 110 ml of absolute N,N-dimethylformamide (DMF) were reacted by the same procedure as described in Example 18. The subsequent stirring time was 2 hours at 90° C. and 7 hours at 105° C. The DMF was then removed by distillation in vacuo. The residue remaining was taken up in $CH_2Cl_2$/water. After thorough mixing, the phases were separated, the aqueous solution was extracted a further three time with $CH_2Cl_2$, and the $CH_2Cl_2$ extracts were combined and, after drying using $MgSO_4$, were evaporated in vacuo. The residue was mixed with 70 ml of $CH_2Cl_2$, and the substance produced in crystalline form during this procedure was filtered off under suction. This solid (1.7 g) was 1,2-dihydro-4-(4-tolyl)phthalazin-1-one, a by-product. The filtrate was concentrated to a volume of 40–50 ml, whereupon further substance crystallized out, which was filtered off under suction. This component (4.65 g) was boiled briefly with 15 ml of methanol, and, after cooling (<10° C.), filtered off under suction and dried. At this point, 2.72 g of pure 1-(4-hydroxyphenyl)-4-[4-(4-tolyl)phthalazin-1-yl]piperazine, melting point 265°–66° C., were obtained, analysis: $C_{25}H_{24}N_4O$ (MW 396.50). calc. C, 75.73; H, 6.10; N, 14.13; found C, 76.0; H, 6.2; N, 14.2%.

The mother liquors (filtrates) were combined, evaporated in vacuo and chromatographed on a silica gel/$CH_2Cl_2$ column (diameter 4.2 cm, height 38 cm) with elution using $CH_2Cl_2$ and $CH_2Cl_2$/$C_2H_5OH$ mixtures (0.5–10.0% by volume of $C_2H_5OH$). A further 2.9 g of concentrated substance, which, after boiling with 8 ml of methanol, filtering off under suction when cool and drying, produced a further 2.0 g of pure substance, were produced from this procedure. The yield was 4.72 g (=34% of theory) of 1-(4-hydroxyphenyl)-4-[4-(4-tolyl)phthalazin-1-yl]piperazine.

EXAMPLE 20

A mixture of 6.82 g (20 mmol) of 1-(4-hydroxyphenyl)piperazine dihydrobromide, 3.36 g (18.5 mmol) of 2-chloro-5-trifluoromethylpyridine, 2.91 g (21 mmol) of powdered $K_2CO_3$ and 76 ml of absolute DMF was warmed to 80° C., and 460 mg of powdered $K_2CO_3$ were added with stirring at 80° C. in each case after 10 minutes, after a further 25 minutes and after a further 60 minutes (a total of 1.38 g (10 mmol) of $K_2CO_3$), and the mixture was stirred for a further 9 hours at 80° C. After removing the DMF by distillation in vacuo, the residue was taken up in $CH_2Cl_2$/water, the phases were separated after thorough mixing, and the aqueous solution was extracted three times with $CH_2Cl_2$. The combined $CH_2Cl_2$ extracts were dried, filtered and evaporated in vacuo. The residue (6 g) was dissolved in boiling methanol. The turbid solution formed was filtered through kieselguhr under suction, concentrated to half the volume, and cooled in an ice bath. The crystals which precipitated out were filtered off under suction and dried. The filtrate, after further concentration and cooling, precipitated further crystalline substance, which was filtered off under suction and recrystallized from a little methanol. In this fashion, 3.43 g (=57.4% yield) of 1-(4-hydroxyphenyl)-4-(5-trifluoromethylpyrid-2-yl)piperazine, melting point 178°–79° C., were obtained.

analysis: $C_{16}H_{16}F_3N_3O$ (MW 323.33) calc. C, 59.44; H, 4.99; N, 13.0; found C, 59.0; H, 5.2; N, 13.1%.

EXAMPLE 21

2.21 g (6 mmol) of 1-(4-hydroxy-3,5-dimethylphenyl)-piperazine dihydrobromide, 1.14 g (6.25 mmol) of 2-chloro-5-trifluoromethylpyridine and 1.245 g (9 mmol) of $K_2CO_3$ in 27 ml of absolute DMF were reacted by the same procedure as described in Example 20. The mixture was subsequently stirred for 3.5 hours at 90° C. After evaporation of the DMF, the residue was mixed with water, and the oily crystalline material produced during this was filtered off under suction, dissolved in methanol and clarified using activated charcoal. After filtration, a little water was added to the filtrate, a crystalline precipitate being produced. This was filtered off under suction (yield 1.63 g) and chromatographed as described in Example 15 on a silica gel/$CH_2Cl_2$ column (diameter 2.0 cm, height 22 cm). In this fashion, 1.24 g (=59% yield) of 1-(4-hydroxy-3,5-dimethylphenyl)-4-(5-trifluoromethylpyrid-2-yl)piperazine, melting point 143°–44° C., were obtained;

analysis: $C_{18}H_{20}F_3N_3O$ (MW 351.38) calc. C, 61.53; H, 5.74; N, 11.96; found C, 61.3; H, 5.6; N, 12.1%.

EXAMPLE 22

12.26 g (36 mmol) of 1-(4-hydroxyphenyl)piperazine dihydrobromide, 8.24 g (36.1 mmol) of 2-chloro-3-cyano-4-methyl-6-phenylpyridine and 7.46 g (54 mmol) of powdered $K_2CO_3$ in 135 ml of absolute DMF were reacted at 90° C. according to the procedure described in Example 20. The mixture was subsequently stirred for 10 hours at 110° C. After removal of the DMF by distillation, the residue was taken up in $CH_2Cl_2$/water. After thorough mixing, separating the phases and extraction of the aqueous solution, the $CH_2Cl_2$ extracts were combined, dried and evaporated. The crystalline residue (14.6 g) was recrystallized three times as follows. The substance was dissolved in a boiling mixture of $CH_2Cl_2/CH_3OH$ 1:1, and the majority of the $CH_2Cl_2$ was then removed by distillation. A product crystallized out of the $CH_3OH$ solution obtained, and was filtered off under suction and again recrystallized in this fashion. Further impure substance was isolated from the mother liquors by concentration etc, and this was finally recrystallized again as described above. In this fashion, 6.82 g (=51% yield) of 1-(4-hydroxyphenyl)-4-(3-cyano-4-methyl-6-phenylpyrid-2-yl)piperazine, melting point 207°-08° C., were obtained;

analysis: $C_{23}H_{22}N_4O$ (MW 370.46) calc. C, 74.57; H, 5.99; N, 15.12; found C, 73.7; H, 5.9; N, 14.9%.

EXAMPLE 23

A mixture of 12.77 g (37.5 mmol) of 1-(4-hydroxyphenyl)piperazine dihydrobromide, 7.13 g (37.6 mmol) of 2-chloro-6-phenylpyridine, 8 g (58 mmol) of $K_2CO_3$ and 145 ml of absolute DMF were refluxed for 24 hours with stirring. The DMF was then removed by distillation in vacuo. $CH_2Cl_2$/water was added to the residue, the mixture was shaken thoroughly, the phases were separated, and the aqueous solution was extracted repeatedly with $CH_2Cl_2$. After drying and filtering, the combined $CH_2Cl_2$ extracts were evaporated. The residue was taken up in ethyl acetate, whereupon a crystalline precipitate was produced, which was filtered off under suction. This solid (4.89 g) was a byproduct, to be precise 1-(4-hydroxyphenyl)-4-formylpiperazine. The ethyl acetate solution (filtrate) was evaporated, and the residue remaining (12 g) was chromatographed on a silica gel/$CH_2Cl_2$/petroleum ether 1:2 column (diameter 2.2 cm, height 44 cm). Elution was effected using $CH_2Cl_2$/petroleum ether 1:2, 1:1 and 2:1 mixtures, with $CH_2Cl_2$, and with $CH_2Cl_2/C_2H_5OH$ mixtures (0.5-2.0% by volume of $C_2H_5OH$). After preliminary fractions, 2.82 g (=22.7% yield) of 1-(4-hydroxyphenyl)-4-(6-phenylpyrid-2-yl)piperazine were obtained as a highly viscous oil;

analysis: $C_{21}H_{21}N_3O$ (MW 331.42) calc. C, 76.11; H, 6.39; N, 12.68; found C, 75.7; H, 6.2; N, 12.3%.

EXAMPLE 24

By the same procedure as described in Example 23, on a 25 mmol scale, starting from 1-(4-hydroxyphenyl)-piperazine dihydrobromide, $K_2CO_3$ and 2-chloro-6-cyclohexyl-4-methylpyridine (34 hours refluxing with stirring) in absolute DMF with addition of 5 mmol of sodium iodide, 1-(4-hydroxyphenyl)-4-(6-cyclohexyl-4-methylpyrid-2-yl)piperazine, melting point 82°-83° C., was prepared in 15% yield;

analysis: $C_{22}H_{29}N_3O$ (MW 351.50) calc. C, 75.18; H, 8.32; N, 11.96; found C, 73.5; H, 8.5; N, 11.6%.

Under these reaction conditions, the main product is 1-(4-hydroxyphenyl)-4-formylpiperazine, which is produced as an undesired product in 74% yield.

We claim:

1. A compound of the formula I

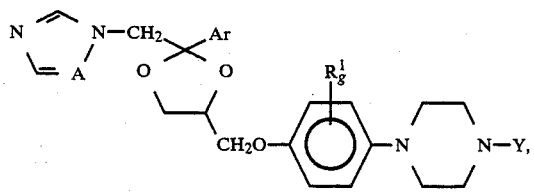

in which
A denotes CH or N,
Ar denotes napthyl, thienyl, halothienyl or a phenyl group which is unsubstituted or carries one to 3 substituents, where the substituents may be identical or different and denote halogen, trifluoromethyl, $C_1-C_2$-alkyl, $C_1-C_2$-alkoxy or phenoxy,
$R^1$ denotes $C_1-C_3$-alkyl, F or Cl,
g denotes 0, 1 or 2, and
Y denotes the following heterocyclic radicals

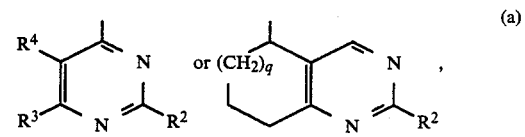

(a)

in which $R^2$ denotes $C_1-C_4$-alkyl, a phenyl group which is unsubstituted or carries 1 or 2 substituents, where the substituents may be identical or different and denote halogen, trifluoromethyl, methoxy, ethoxy, nitro or $C_1-C_4$-alkyl, or a phenyl-$C_1-C_2$-alkyl group which is unsubstituted or carries 1 or 2 substituents in the phenyl radical, where the substituents may be identical or different and denote F, Cl, methoxy, ethoxy or $C_1-C_3$-alkyl,
$R^3$ denotes H, $C_1-C_8$-alkyl, $C_3-C_6$-cycloalkyl-$C_1-C_3$-alkyl, a phenyl group which is unsubstituted or carries 1 or 2 substituents, where the substituents may be identical or different and denote halogen, methoxy, ethoxy or $C_1-C_3$-alkyl, a phenyl-$C_1-C_2$-alkyl group which is unsubstituted or substituted in the phenyl radical by methoxy, 1,2-methylenedioxy, F, Cl or $C_1-C_3$-alkyl, or trifluoromethyl,
$R^4$ denotes H, $C_1-C_4$-alkyl or benzyl, or $R^3$ and $R^4$ together denote $-(CH_2)_r-$, where r is 3 or 4, or $-CH=CH-CH=CH-$, and
q denotes 0 or 1,
and the physiologically acceptable acid-addition salts thereof.

2. Compound I as claimed in claim 1, wherein at least one of the substituents has the following meaning:
A denotes CH or N,
Ar denotes a phenyl group which is substituted by 1 or 2 F or Cl atoms,
$R^1$ denotes $CH_3$ or $C_2H_5$,
g denotes 0 or 2, and
where Y denotes the heterocyclic radical (a),
$R^2$ denotes $C_1-C_4$-alkyl, a phenyl group which is unsubstituted or carries 1 or 2 identical or different substituents, where the substituents denote F, Cl, $OCH_3$, $OC_2H_5$, $CH_3$ or $C_2H_5$, or denotes a benzyl group or a benzyl group which is substituted in the phenyl radical by an F or Cl atom,
$R^3$ denotes $C_1-C_8$-alkyl, $C_5-C_6$-cycloalkyl-$C_1-C_2$-alkyl, or a phenyl group or a phenyl-$C_1-C_2$-alkyl group which is in each case unsubstituted or substituted in the phenyl radical by 1 or 2 F, Cl, $OCH_3$ or $CH_3$, or $CF_3$,
$R^4$ denotes $C_1-C_4$-alkyl or benzyl, or
$R^3$ and $R^4$ together denote $-(CH_2)_3-$, $-(CH_2)_4-$ or $-CH=CH-CH=CH-$, and
q denotes 0 or 1.

3. Compound I as claimed in claim 1, wherein at least one of the substituents or indices has the following meaning:
A denotes CH or N, Ar denotes 2,4-dichlorophenyl,
R$^1$ denotes CH$_3$,
g denotes 0 or 2, and
where Y denotes a heterocyclic radical (a),
- R$^2$ denotes a phenyl group which is unsubstituted or carries 1 or 2 identical or different substitutents, where the substituents denote Cl, OCH$_3$, OC$_2$H$_5$ or CH$_3$, or denotes benzyl group or a chlorobenzyl group,
- R$^3$ denotes C$_1$-C$_8$-alkyl, C$_5$-C$_6$-cycloalkyl-C$_1$-C$_2$-alkyl, or a phenyl group or phenyl-C$_1$-C$_2$-alkyl group, in each case unsubstituted or substituted in the phenyl radical by 1 or 2 F, Cl, OCH$_3$ or CH$_3$,
- R$^4$ denotes C$_1$-C$_4$-alkyl or benzyl, or
- R$^3$ and R$^4$ together denote —(CH$_2$)$_3$—, —(CH$_2$)$_4$— or —CH=CH—CH=CH—, and
- q denotes 0 or 1.

4. A compound I as claimed in claim 1, wherein the azolylmethyl radical and the piperazinophenoxymethyl group in the 4 position on the dioxolane ring are in the cis position.

5. A pharmaceutical composition having an antimycotic action, containing an active amount of a compound I as claimed in claim 1.

6. A method for the treatment of mycosis, wherein an active amount of a compound I as claimed in claim 1 is administered together with pharmaceutically acceptable excipients.

* * * * *